(12) United States Patent
Garcia-Bennett et al.

(10) Patent No.: US 10,273,453 B2
(45) Date of Patent: Apr. 30, 2019

(54) METHOD FOR STEM CELL DIFFERENTIATION IN VIVO BY DELIVERY OF MORPHOGENES WITH MESOPOROUS SILICA AND CORRESPONDING PHARMACEUTICAL ACTIVE INGREDIENTS

(71) Applicant: Nanologica AB, Stockholm (SE)

(72) Inventors: Alfonso E. Garcia-Bennett, Stockholm (SE); Elena Nickolaevna Kozlova, Stockholm (SE)

(73) Assignee: Nanologica AB (SE)

( * ) Notice: Subject to any disclaimer, the term of this patent is extended or adjusted under 35 U.S.C. 154(b) by 37 days.

(21) Appl. No.: 15/340,537

(22) Filed: Nov. 1, 2016

(65) Prior Publication Data

US 2017/0145382 A1 May 25, 2017

Related U.S. Application Data

(62) Division of application No. 13/808,809, filed as application No. PCT/EP2011/061377 on Jul. 6, 2011, now abandoned.

(60) Provisional application No. 61/361,741, filed on Jul. 6, 2010.

(51) Int. Cl.

| *C12N 5/00* | (2006.01) |
| *C12N 5/0793* | (2010.01) |
| *A61K 9/51* | (2006.01) |
| *A61K 31/00* | (2006.01) |
| *A61K 31/203* | (2006.01) |
| *A61K 38/18* | (2006.01) |
| *A61K 38/17* | (2006.01) |
| *A61K 35/30* | (2015.01) |
| *A61K 35/545* | (2015.01) |
| *A61K 31/5377* | (2006.01) |
| *A61K 47/02* | (2006.01) |
| *A61K 9/16* | (2006.01) |

(52) U.S. Cl.
CPC .......... *C12N 5/0619* (2013.01); *A61K 9/1611* (2013.01); *A61K 9/5115* (2013.01); *A61K 31/00* (2013.01); *A61K 31/203* (2013.01); *A61K 31/5377* (2013.01); *A61K 35/30* (2013.01); *A61K 35/545* (2013.01); *A61K 38/1709* (2013.01); *A61K 38/185* (2013.01); *A61K 47/02* (2013.01); *C12N 2500/38* (2013.01); *C12N 2500/46* (2013.01); *C12N 2501/998* (2013.01); *C12N 2506/02* (2013.01); *C12N 2506/08* (2013.01); *C12N 2533/00* (2013.01)

(58) Field of Classification Search
CPC .............................. C12N 5/0619; A61K 9/5115
See application file for complete search history.

(56) References Cited

U.S. PATENT DOCUMENTS

| 2005/0019801 A1 | 1/2005 | Rubin et al. |
| 2007/0031966 A1 | 2/2007 | Dressler et al. |
| 2007/0160639 A1 | 7/2007 | Pantelidis et al. |
| 2010/0055167 A1 | 3/2010 | Zhang et al. |

FOREIGN PATENT DOCUMENTS

| WO | 2008002250 | 3/2008 |
| WO | 2009100128 | 8/2009 |
| WO | 2009101110 | 8/2009 |
| WO | 2009145761 | 12/2009 |

OTHER PUBLICATIONS

Li et al. Stem Cells 26:886-893, 2008.*
Dominique Bocking, et al., Mesoporous silica nanoparticle-based substrates for cell directed delivery of Notch signaling modulators to control myoblast differentiation, The Royal Society of Chemistry, 2014, 1490-1498.
Alfonso E. Garcia-Bennett, et al., In vitro generation of motor neuron precursors from mouse embryonic stem cells using mesoporous nanoparticles, Nanomedicine, 2014, 2457-2466, vol. 9, No. 16, Future Medicine Ltd.
Sung-Hwan Moon, et al., Differentiation of hESCs into Mesodermal Subtypes: Vascular-, Hematopoietic- and Mesenchymal-lineage Cells, International Journal of Stems Cells, 2011, 24-34, vol. 4, No. 1.
Ligui Pasqua, et al., Preparation of bifunctional hybrid mesoporous silica potentially useful for drug targeting, Microporous and Mesoporous Materials, Jun. 20, 2007, 166-173, vol. 103, No. 1-3, Elsevier Science Publishing, New York.
Xuetao Shi, et al., In-vitro osteogeesis of Synovium stem cells induced by controlled release of bisphosphate additives from microspherical mesoporous silica composite, Biomaterials, Aug. 1, 2009, 3996-4005, vol. 30, No. 23-24, Elsevier Science Publishers BV, Barking GB.
Karl G. Sylvester, et al., Stem Cells, Arch Surg, Jan. 2004, 93-94, vol. 139.
EPO Office Action dated Mar. 15, 2016 in Application No. EP20110745497.

* cited by examiner

Primary Examiner — Marcia S Noble
(74) Attorney, Agent, or Firm — Kim Winston LLP

(57) ABSTRACT

A pharmaceutical active ingredient for cell differentiation to alleviate cell and cell-related deficiencies in mammals comprising porous silica containing a releasable agent capable of contributing to a cell environment conducive for stem cell differentiation in co-implanted stem cells and/or in endogenous stem cells.

16 Claims, 9 Drawing Sheets

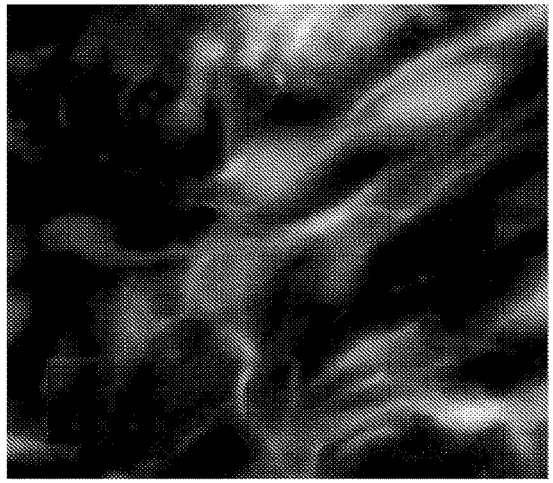
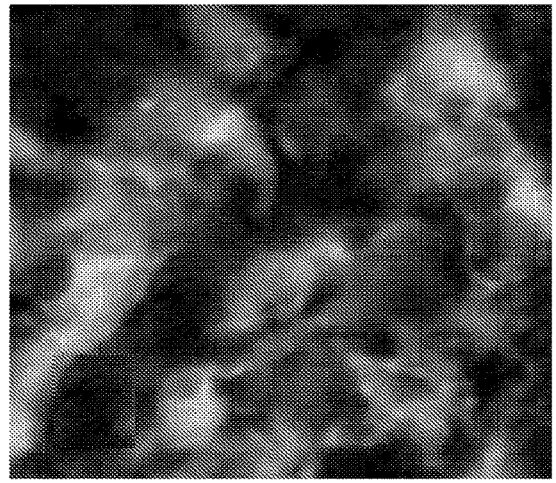
Fig. 3A                    Fig. 3B
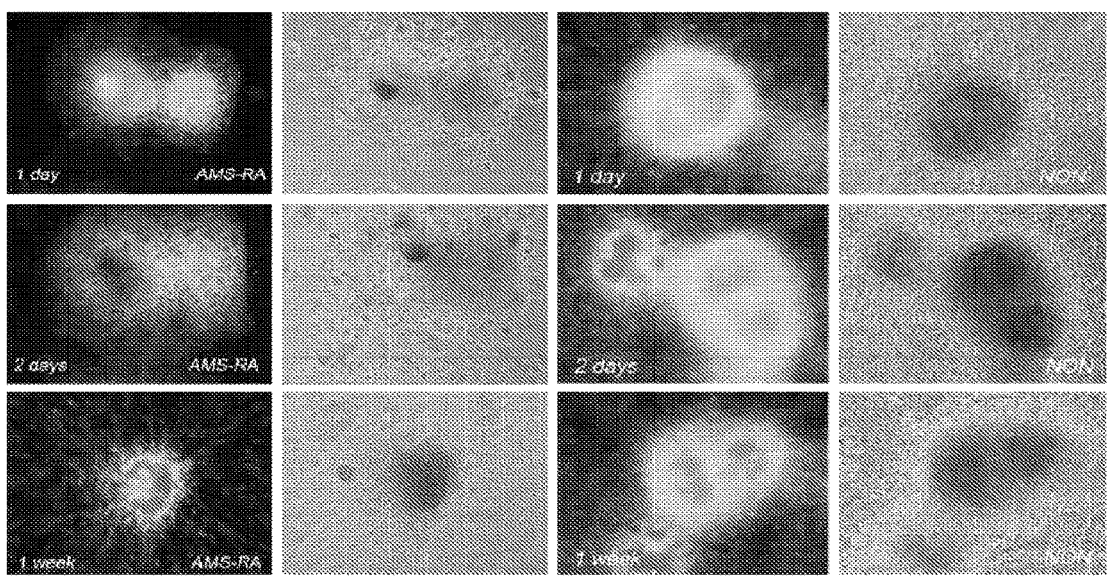
Fig. 4A          Fig. 4B          Fig. 4C          Fig. 4D

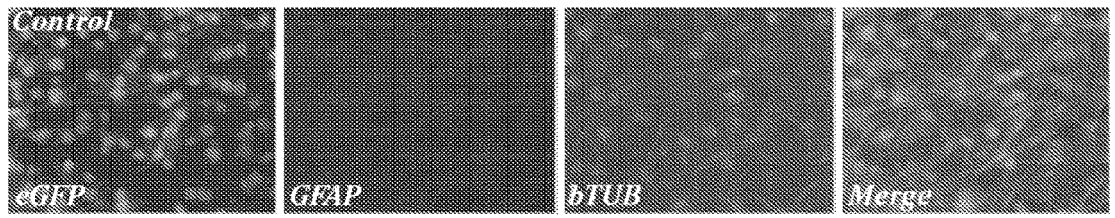
Fig. 5A(i)
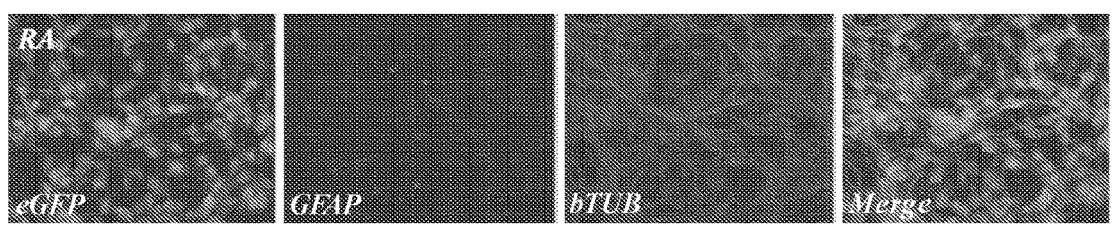
Fig. 5A(ii)
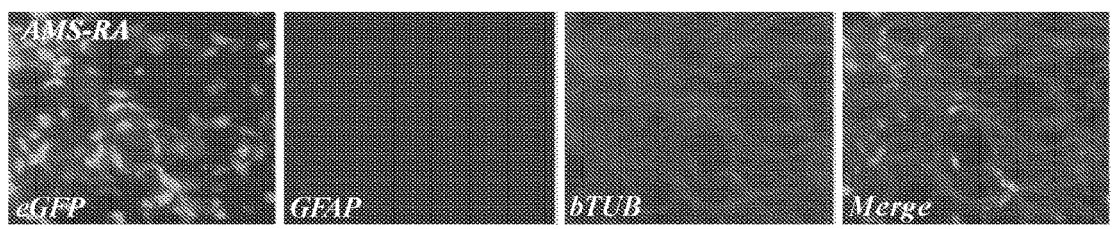
Fig. 5A(iii)
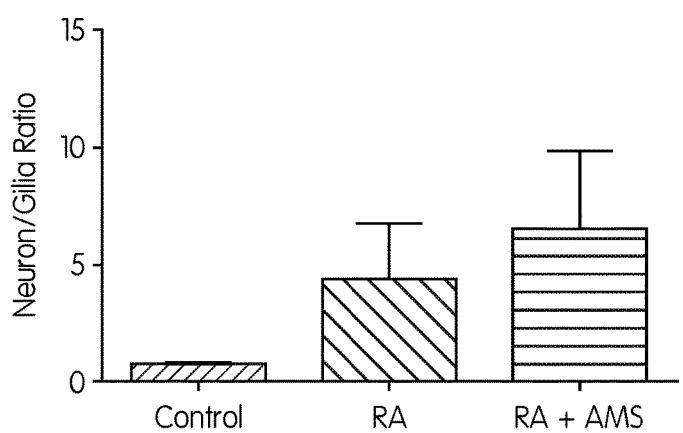
Fig. 5B

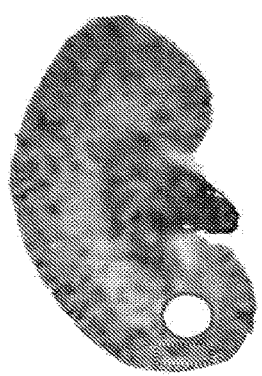
Fig. 7A
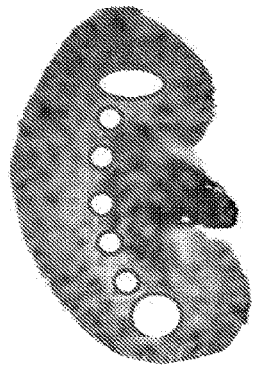
Fig. 7B
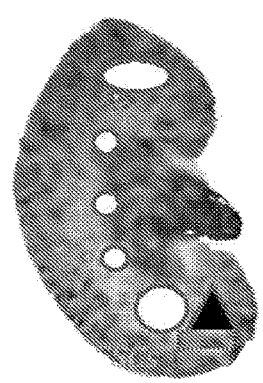
Fig. 7C
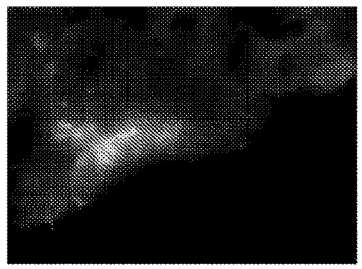
Fig. 8A(i)
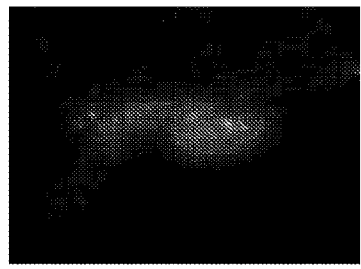
Fig. 8A(ii)
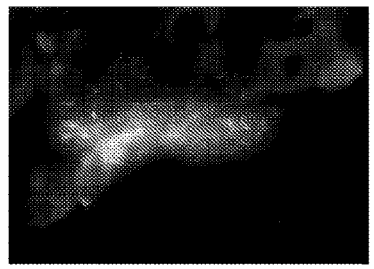
Fig. 8A(iii)
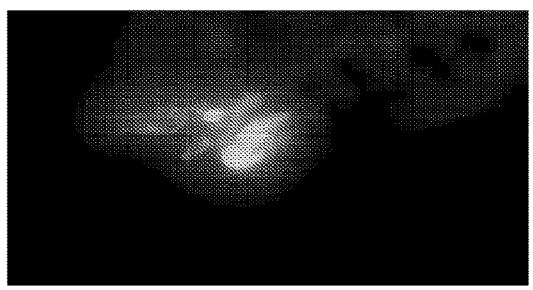
Fig. 8B(i)
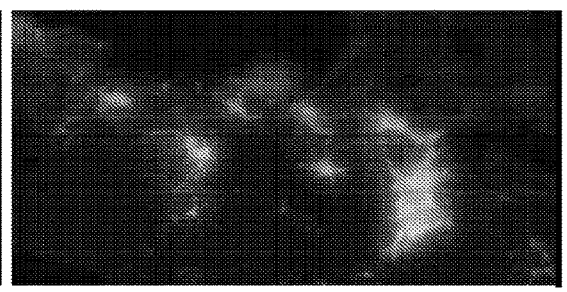
Fig. 8B(ii)

METHOD FOR STEM CELL DIFFERENTIATION IN VIVO BY DELIVERY OF MORPHOGENES WITH MESOPOROUS SILICA AND CORRESPONDING PHARMACEUTICAL ACTIVE INGREDIENTS

CROSS-REFERENCE TO RELATED APPLICATIONS

This application is a divisional of U.S. patent application Ser. No. 13/808,809 filed Jul. 23, 2013 which is a national phase application under 35 U.S.C. § 371 of International Application No. PCT/EP2011/061377 filed on Jul. 6, 2011, which claims the benefit of U.S. Provisional Patent Application No. 61/361,741 filed on Jul. 6, 2010, the entire disclosures of which are hereby incorporated by reference in their entirety.

DESCRIPTION

Field of the Invention

The present invention relates to pharmaceutical active ingredients comprising sets composed of stem cells and porous silica, preferably mesoporous silica, containing a defined set of differentiation factors for desired differentiation of different types of cells, and to a method of enhancing survival and control differentiation of transplanted stem cells for regenerative medicine by providing said sets. In particular, the pharmaceutical active ingredients and methods of the invention are preferably used for controlling differentiation of embryonic stem cells (ESCs) and induced pluripotent stem cells (iPSCs); in general, they are also applicable for other stem cells, e.g. tissue-specific stem cells and mesenchymal stem cells.

Background of the Invention

Experimental stem cell research has achieved enormous progress during the past few years in generating desired types of cells in vitro, which can be used in regenerative medicine. These in vitro protocols have confirmed that extrinsic factors/morphogens may induce expression of specific transcription factors (TFs), which establish molecular codes for the identity of stem cell differentiation. The identification of extrinsic factors which transduce their effects through TF codes in stem cell differentiation and exploration of this information for the development of delivery systems for these factors to the transplanted stem cells may result in translation of in vitro protocols to in vivo applications. A method to control stem cell differentiation after transplantation by controlled expression of TFs in the transplanted cells using drug-inducible regulation systems is described in patent application WO2008/002250, having title "Improved Stem Cells For Transplantation And Methods For Production Thereof".

Stem cell transplantation is an attractive strategy for replacement of specific cells that are permanently lost or non-functional as a result of injury or disease. Transplanted stem cells can also promote tissue repair through trophic and cell protective effects, i.e. without replacing the specific cells that have been lost by injury or disease. While such "unspecific" effects may be beneficial and important, the ultimate goal of stem cell transplantation still remains to replace the damaged or diseased cells with fully functional cells of the same type. The environment that transplanted stem/progenitor cells will meet is predominantly adult and marked by pathological responses. For cell replacement therapy to be successful, it is important to understand these responses and how they can either be modified to provide a host environment which is compatible with long term survival and the desired differentiation or how this environment can be changed, so that the transplanted cells will be unaffected by negative external stimuli.

The results from numerous in vitro and in vivo experiments have convincingly demonstrated that the timely expression of certain cell-intrinsic factors, transcription factors, during normal development or during stem cell differentiation in vitro can be sufficient to induce and in some cases to guide differentiation of stem cells. Using the tetracycline gene regulation system to induce the expression of the key transcription factor Runx1 in Sox10 expressing neural crest stem cells we achieved specific differentiation of nociceptor neurons in vitro and in vivo after transplantation (Aldskogius H, Berens C, Kanaykina N, et al. Regulation of boundary cap neural crest stem cell differentiation after transplantation. Stem Cells 2009; 27:1592-603). In order to achieve such a timely expression of cell-intrinsic and transcription factors it is hence desired to achieve the kinetic release of gene regulating molecules through the use of a delivery vehicle.

Another possibility to promote tissue protection and/or stem cell differentiation after transplantation is to create a suitable environment for transplanted cells. This can be achieved by co-transplantation of supporting cells or the use of osmotic minipumps that provide substances for improved survival, differentiation and function of transplanted cells. Co-transplantation of neural crest stem cells with pancreatic islets showed beneficial effects for both islets and stem cells with improved insulin secretion, increased proliferation of beta-cells and advanced differentiation of neural crest stem cells in the vicinity of islets (Olerud J, Kanaykina N, Vasylovska S, et al. Neural crest stem cells increase beta cell proliferation and improve islet function in co-transplanted murine pancreatic islets. Diabetologia 2009; 52:2594-601. Erratum in: Diabetologia. 2010; 53:396. Vasilovska, S [corrected to Vasylovska, S]).

As for the delivery, porous particles have been developed for pharmaceutical drug delivery due to their potential to control (delay) drug release, enhance drug dissolution, promote drug permeation across the intestinal cell wall (bioavailability) and improve drug stability under the extreme environment of the gastro-intestinal tract when administered orally (Vallhov H, Gabrielsson S, Strømme M, et al. Mesoporous silica particles induce size dependent effects on human dendritic cells. Nano Lett 2007; 7:3576-82; Fadeel B, Garcia-Bennett A E. Better safe than sorry: Understanding the toxicological properties of inorganic nanoparticles manufactured for biomedical applications. Adv Drug Deliv Rev 2010; 62:362-74).

External Factors for Cell Differentiation

Nearly all developmental decisions during embryogenesis are regulated by a relatively small number of families of secreted growth factors and morphogens, including fibroblast growth factors (FGFs) (Böttcher RT, Niehrs C. Fibroblast growth factor signaling during early vertebrate development. Endocr Rev 2005; 26:63-77), Wnts (Logan C Y, Nusse R. The Wnt signaling pathway in development and disease. Annu Rev Cell Dev Biol 2004; 20:781-810), transforming growth factor (TGF)-beta family members (Massagué J. TGF-beta signal transduction. Annu Rev Biochem 1998; 67:753-91), and Hedgehog (hh) proteins (McMahon A P, Ingham P W, Tabin C J. Developmental roles and clinical significance of hedgehog signaling. Curr Top Dev Biol 2003; 53:1-114). The first clues to the molecular nature of the organizer's (signals from a region of dorsal mesoderm) inductive influence came from studies of a receptor for TGF-beta superfamily members, and Noggin, a secreted factor expressed by the organizer (Hemmati-Brivanlou A, Melton D A, A truncated activin receptor inhibits mesoderm induction and formation of axial structures in *Xenopus* embryos. Nature 1992; 359:609-14; Smith W C, Harland R M. Expression cloning of noggin, a new dorsalizing factor localized to the Spemann organizer in *Xenopus* embryos. Cell 1992; 70:829-40; Lamb T M, Knecht A K, Smith W C, et al. Neural induction by the secreted polypeptide noggin. Science 1993; 262:713-8). Embryonic stem (ES) cells differentiate to neural stem cells based on FGF4/Notch treatment followed by the FGF/epidermal growth factor (EGF) treatment are described in www.cscr.camn.ac.uk/asmith.html. The stem cell signaling network, and specifically the Wnt, Notch, FGF, and BMP signaling cascades, are implicated in the regulation of the balance for neural stem cells, progenitor cells, and differentiated neural cells (Israsena N, Hu M, Fu W, et al. The presence of FGF2 signaling determines whether beta-catenin exerts effects on proliferation or neuronal differentiation of neural stem cells. Dev Biol 2004:268:220-31; Akai J, Halley P A, Storey K G. FGF-dependent Notch signaling maintains the spinal cord stem zone. Genes Dev 2005; 19:2877-87).

Sonic Hedgehog (Shh)

Shh plays a prominent role in the patterning of the developing neural tube (Lee K J, Jessell T M. The specification of dorsal cell fates in the vertebrate central nervous system. Annu Rev Neurosci 1999; 22:261-94; Tanabe Y, Jessell T M. Diversity and pattern in the developing spinal cord. Science 1996; 274:1115-23. Review. Erratum in: Science 1997; 276:21). Ectopic application of Shh is sufficient to induce formation of motor neurons in the dorsal neural tube (Ericson J, Morton S, Kawakami A, et al. Two critical periods of Sonic Hedgehog signaling required for the specification of motor neuron identity. Cell 1996; 87:661-73; Ericson J, Muhr J, Placzek M, et al. Sonic hedgehog induces the differentiation of ventral forebrain neurons: a common signal for ventral patterning within the neural tube. Cell 1995; 81:747-56. Erratum in: Cell 1995; 82:following 165) and in culture (Hu B Y, Zhang S C. Differentiation of spinal motor neurons from pluripotent human stem cells. Nat Protoc 2009; 4:1295-304). Shh both patterns cell fates along the dorso-ventral axis of the spinal cord and regulates cell number through its effects on proliferation and programmed cell death (Ericson J, Morton S, Kawakami A, et al. Two critical periods of Sonic Hedgehog signaling required for the specification of motor neuron identity. Cell 1996; 87:661-73; Oppenheim R W, Homma S, Marti E, et al. Modulation of early but not later stages of programmed cell death in embryonic avian spinal cord by sonic hedgehog. Mol Cell Neurosci 1999; 13:348-61).

Shh promotes neural crest proliferation (Fu M, Lui V C, Sham M H, Pachnis V, et al. Sonic hedgehog regulates the proliferation, differentiation, and migration of enteric neural crest cells in gut. J Cell Biol 2004; 166:673-84) and survival (Ahlgren S C, Bronner-Fraser M. Inhibition of sonic hedgehog signaling in vivo results in craniofacial neural crest cell death. Curr Biol 1999; 9:1304-14; Ahlgren S C, Thakur V, Bronner-Fraser M. Sonic hedgehog rescues cranial neural crest from cell death induced by ethanol exposure. Proc Natl Acad Sci USA 2002; 99:10476-81) in addition to regulating neural crest motility (Testaz S, Jarov A, Williams K P, et al. Sonic hedgehog restricts adhesion and migration of neural crest cells independently of the Patched-Smoothened-Gli signaling pathway. Proc Natl Acad Sci USA 2001; 98:12521-6). Furthermore Shh promotes both cell proliferation and programmed cell death (PCD) of early dorsal root ganglion (DRG) cells thus regulating DRG cell number, the distribution of sensory phenotypes and sensory path finding (Guan W, Wang G, Scott S A, et al. Shh influences cell number and the distribution of neuronal subtypes in dorsal root ganglia. Dev Biol 2008; 314:317-28).

Retinoic Acid (RA)

Retinoic acid is another signaling molecule with pronounced effect on differentiation and survival of developing vertebrate CNS neurons (Maden, M. Retinoid signalling in the development of the central nervous system. Nat Rev Neurosci 2002; 3:843-53; Appel B, Eisen J S. Retinoids run rampant: multiple roles during spinal cord and motor neuron development. Neuron 2003; 40:461-4). Retinoic acid can stimulate both neurite number and neurite length (Maden, M. Role and distribution of retinoic acid during CNS development. Int Rev Cytol 2001; 209:1-77); and is implicated in the regeneration of injured peripheral nerve (Zhelyaznik N, Schrage K, McCaffery P, et al. Activation of retinoic acid signaling after sciatic nerve injury: up-regulation of cellular retinoid binding proteins. Eur J Neurosci 2003; 18:1033-40). In embryonic DRG neurons, RARb2 mediates neurite outgrowth induced by retinoic acid (Corcoran J, Shroot B, Pizzey J, et al. The role of retinoic acid receptors in neurite outgrowth from different populations of embryonic mouse dorsal root ganglia. J. Cell Sci 2000; 113:2567-74). Recently was demonstrated that induced expression of RAR-beta2 in adult DRG neurons is sufficient to drive growth of their axons through the non-permissive interface between the dorsal root and the spinal cord, the dorsal root transitional zone (DRTZ) and into the spinal cord (Wong L F, Yip P K, Battaglia A, et al. Retinoic acid receptor beta2 promotes functional regeneration of sensory axons in the spinal cord. Nat Neurosci 2006; 9:243-50).

Wnt

Another group of molecules implicated in orchestrating embryogenesis are the Wnt family members. FZD1, FZD2, FZD3, FZD4, FZD5, FZD6, FZD7, FZD8, FZD9, FZD10, LRP5, LRP6, and ROR2 are transmembrane receptors transducing Wnt signals based on ligand-dependent preferentiality for caveolin- or clathrin-mediated endocytosis. Wnt signals are transduced to canonical pathway for cell fate determination, and to non-canonical pathways for regulation of planar cell polarity, cell adhesion, and motility. Thus for canonical Wnt signaling cascade MYC, CCND1, AXIN2, FGF20, WISP1, JAG1, DKK1 and glucagon are target genes, while CD44, vimentin and STX5 are target genes of non-canonical Wnt signaling cascades.

The target genes of Wnt signaling cascades are dependent on the expression profile of transcription factors and epigenetic status. Wnt signaling cascades associated with Notch, FGF, BMP and Hedgehog signaling cascades regulate the balance of mesenchymal stem cells, hematopoietic stem cells, and intestinal stem cells and their progenitor cells. Wnt3, Wnt5A and Wnt10B are expressed in undifferentiated human embryonic stem cells, whereas Wnt6, Wnt8B and Wnt10B are expressed in endoderm precursor cells. Wnt6 is expressed in the intestinal crypt region for stem or progenitor cells. TNF/alpha-Wnt10B signaling maintains homeostasis of adipose tissue and gastrointestinal mucosa with chronic inflammation. Recombinant Wnt protein or Wnt mimetic (circular peptide, small molecule compound, or RNA aptamer) in combination with Notch mimetic, FGF, and BMP (Katoh M. WNT signaling in stem cell biology and regenerative medicine. Curr Drug Targets 2008; 9:565-70) open a new window to mesoporous silica application in regulation of stem cell differentiation. The Wnt signaling pathway is critically important for organogenesis and the development of the body plan. Beta-catenin/TCF7L2-dependent Wnt signaling (the canonical pathway) is involved in pancreas development, islet function, and insulin production and secretion. The glucoincretin hormone glucagon-like peptide-1 and the chemokine stromal cell-derived factor-1 modulate canonical Wnt signaling in beta-cells which is obligatory for their mitogenic and cytoprotective actions. The transcription factor TCF7L2 is particularly strongly associated with a risk for diabetes and appears to be fundamentally important in both canonical Wnt signaling and beta-cell function.

An inhibitory role for Wnts is shown in a repressive function for Wnt signaling in mouse neural induction. Mouse mutants lacking effectors of b-catenin-dependent Wnt signaling, such as Wnt3a, display increased neural tissue and even ectopic neural tubes (Yoshikawa Y, Fujimori T, McMahon A P, et al. Evidence that absence of Wnt-3a signaling promotes neutralization instead of paraxial mesoderm development in the mouse. Dev Biol 1997; 183:234-42). Similarly, mutation of the Wnt co-receptors Lrp5 and Lrp6 results in an expansion of the anterior neuroectoderm (Kelly O G, Pinson K I, Skarnes W C. The Wnt co-receptors Lrp5 and Lrp6 are essential for gastrulation in mice. Development 2004; 131:2803-15). Consistent with this negative regulatory role, loss of Dickkopf (Dkk), a Wnt inhibitor, prevents forebrain development (Mukhopadhyay M, Shtrom S, Rodriguez-Esteban C, et al. Dickkopf1 is required for embryonic head induction and limb morphogenesis in the mouse. Dev Cell 2001; 1: 423-34).

Bone Morphogenetic Protein (BMP)

FIG. 1 schematically shows in vitro neural induction. Many in vivo neural inducers that act as inhibitors of BMPs, Nodal and Wnt signaling also promote ES cell differentiation to committed neural cells. In contrast, RA, which promotes neural induction in ESCs, is not known to be important for neural induction in vivo (Gaulden J, Reiter J F. Neur-ons and neur-offs: regulators of neural induction in vertebrate embryos and embryonic stem cells. Hum Mol Genet 2008; 17:R60-6).

Fibroblast Growth Factors (FGFs)

In support of the involvement of FGFs in neural induction, FGFs can act cooperatively with BMP inhibition to promote Xenopus neural induction (Reversade B, Kuroda H, Lee H, et al. Depletion of Bmp2, Bmp4, Bmp7 and Spemann organizer signals induces massive brain formation in Xenopus embryos. Development 2005; 132:3381-92). One possible molecular mechanism for this functional cooperation is through MAPK pathway convergence on BMP signaling through the differential phosphorylation of Smad1, an important BMP effector (Pera E M, Ikeda A, Eivers E, et al. Integration of IGF, FGF, and anti-BMP signals via Smad1 phosphorylation in neural induction. Genes Dev 2003; 17:3023-8). GSK3, a component and inhibitor of the Wnt pathway, promotes additional phosphorylation and degradation of Smad1 after a priming phosphorylation by MAPK, which may similarly explain the anti-neuralizing properties of Wnts (Fuentealba L C, Eivers E, Ikeda A, et al. Integrating patterning signals: Wnt/GSK3 regulates the duration of the BMP/Smad1 signal. Cell 2007; 131:980-93).

However, mutation of the MAPK phosphorylation site of Smad1 does not overtly abrogate neural induction in mice, suggesting that this interaction is not essential for the effects of FGFs on neural induction (Aubin J, Davy A, Soriano P. In vivo convergence of BMP and MAPK signaling pathways: impact of differential Smad1 phosphorylation on development and homeostasis. Genes Dev 2004; 18:1482-94). Another possibility is that early FGF signals downregulate expression of BMPs in the prospective neural domain, allowing neural differentiation to proceed (Wilson S I, Graziano E, Harland R. An early requirement for FGF signalling in the acquisition of neural cell fate in the chick embryo. Curr Biol 2000; 10:421-9; Furthauer M, Van Celst J, Thisse C, et al. Fgf signalling controls the dorsoventral patterning of the zebrafish embryo. Development 2004; 131:2853-64). A third possibility is that early FGF signaling promotes neural fate through a parallel, BMP-independent mechanism (Delaune, E., Lemaire, P. and Kodjabachian, L. Neural induction in Xenopus requires early FGF signalling in addition to BMP inhibition. Development 2005; 132: 299-310; Linker C, Stern C D. Neural induction requires BMP inhibition only as a late step, and involves signals other than FGF and Wnt antagonists. Development 2004:131: 5671-81). One BMP independent mechanism may involve Wnts which, as described above, can inhibit neural induction during gastrulation stages (Wilson S I, Rydstrom A, Trimborn T, et al. (2001) The status of Wnt signaling regulates neural and epidermal fates in the chick embryo. Nature 2001; 411:325-30). However, addition of multiple FGFs, BMP antagonists and Wnt antagonists to the chick embryonic epiblast is not sufficient to induce the expression of the neural marker Sox2, suggesting that still other pathways regulate neural induction (Linker C, Stern C D. Neural induction requires BMP inhibition only as a late step, and involves signals other than FGF and Wnt antagonists. Development 2004:131:5671-81).

Maintenance and Enhancement of Axonal Outgrowth of Differentiated Stem Cells In Vivo Different sets of cues are implicated in the guidance of axonal growth: the "canonical" guidance cues—Netrins, Slits, Semaphorins, and Ephrins (O'Donnell M, Chance R K, Bashaw G J. Axon growth and guidance: receptor regulation and signal transduction. Annu Rev Neurosci. 2009; 32:383-412), the morphogens of the Hedgehog, BMP, and Wnt families, and the cell adhesion molecules such as N-cadherin, NCAM, and LI-CAM (Skaper S D, Moore S E, Walsh F S. Cell signalling cascades regulating neuronal growth-promoting and inhibitory cues. Prog Neurobiol. 2001 December; 65(6):593-608). A combination of these cues working at different ranges exerts fine directional control for axon.

Whereas initial neuronal differentiation of implanted stem cells can be achieved in vivo by exposing them to the appropriate factors described above, optimal survival and efficient axonal outgrowth of these cells is also dependent on the early presence of specific trophic factors in their environment (Lindsay R M, Wiegand S J, Altar C A, DiStefano P S. Neurotrophic factors: from molecule to man. Trends Neurosci. 1994 May; 17(5):182-90). These factors signal through specific receptors expressed by target neurons and regulated their expression of survival and axon outgrowth promoting genes. Thus, the delivery of trophic factors to in vivo implanted stem cells will significantly improve their long term survival and functional integration. The relevant trophic factors include the neurotrophin family (nerve growth factor (NGF), brain-derived neurotrphic factor (BDNF), neurotrophin (NT)3 and NT4/5), the TGF-beta-related family of growth factors (glial cell line-derived neurotrophic factor (GDNF), artermin and persephin) (Airaksinen M S, Saarma M. The GDNF family: signalling, biological functions and therapeutic value. Nat Rev Neurosci. 2002 May; 3(5):383-94), the cytokines ciliary neurotrophic factor (CNTF), leukemia inhibitory factor (LIF), cardiotrophin 1 and oncostatin M (Murphy M, Dutton R, Koblar S, Cheema S, Bartlett P. Cytokines which signal through the LIF receptor and their actions in the nervous system. Prog Neurobiol. 1997 August; 52(5):355-78), and the cerebral dopamine neurotrophic factor and astrocyte-derived neurotrophic factor (CDNF/MANF) family (Lindholm P, Saarma M. Novel CDNF/MANF family of neurotrophic factors. Dev Neurobiol. 2010 April; 70(5):360-71).

BRIEF DESCRIPTION OF THE INVENTION

Small molecules that function as agonists or antagonists of cellular receptors comprise some of the most valuable therapeutic agents and molecular probes. Their controlled long-term delivery to injured, diseased or transplanted tissues can have critical effects on cell differentiation and tissue repair in the target areas. According to the present invention mesoporous silicas with controlled particle size have been prepared using a variety of methods, for example using anionic amino acid-derived amphiphiles and alkoxy silane costructure-directing agents (CSDAs), denoted AMS-n mesoporous silicas (Shunai Che, Alfonso E. Garcia-Bennett, Toshiyuki Yokoi, Kazutami Sakamoto, Hironobu Kunieda, Osamu Terasaki, Takashi Tatsumi. A novel anionic surfactant templating route for synthesizing mesoporous silica with unique structure; Nature Materials, 2003, 2, 801.). Mesoporous materials are used according to the present invention to control stem cell differentiation after transplantation. We evaluated how mesoporous particles, including nanoparticles with well-defined porosity, control the release of the Sonic Hedgehog (Shh) agonist purmorphamin (Pur) and retinoic acid (RA) over extended periods of time affecting stem cell survival, migration and differentiation. We showed that delivery of RA and Pur from AMS-n is effective in promoting neuronal differentiation from embryonic stem cells and regional neural crest stem cells in vitro and in vivo. These findings indicate that porous silica-mediated delivery of cell differentiation factors is a useful and advantageous approach in transplantation and tissue repair strategies.

Thus, according to the present invention, we have used a new approach—the mesoporous silica delivery system for induced differentiation of stem cells in vitro and in vivo after transplantation with extrinsic factors. The combination of both methods—intrinsic and extrinsic factors will facilitate the development of in vivo protocols for controlled and reproducible stem cell differentiation that may be translated to clinical application.

As better shown hereinafter, according to the present invention, porous particles can be employed for controlled delivery of differentiation factors to obtain the desired type of cells from stem cell transplants. In the following description, we will also see the effect of mesoporous on stem cell survival, glial scar formation and migration of stem cells.

To explore the utility of this delivery technology for stem cell differentiation, mesoporous silica with controlled particle and pore size have been prepared using a variety of pore forming templates including surfactants and non-surfactant molecules, for controlled release of purmorphamine, a Sonic Hedgehog (Shh) agonist and retinoic acid (RA) over extended time periods after co-transplantation with bNCSCs, mouse and human embryonic stem cells. The creation of such system, which will provide an in vitro and/or in vivo environment favorable for stem cell survival and differentiation, has great potential for use in developmental biology and stem cell transplantation strategies.

We anticipate that timely delivery of extracellular substances, such as fibroblast growth factors (FGFs), Wnts, transforming growth factor (TGF)-beta family members, and Hedgehog (hh) proteins to transplanted stem/progenitor cells, which are pre-differentiated in vitro before transplantation, can lead to the development of in vivo protocols for controlled stem cell differentiation.

SUMMARY OF THE INVENTION

The present invention relates to a method to stimulate the survival and differentiation of transplanted stem cells by delivery of defined external factors from mesoporous silica. The present invention is, among others, suitable for transplantation of human ESCs and iPSCs, human tissue-specific stem cells and mesenchymal stem cells in a clinic, as well as for experimental systems with corresponding stem cells from other species.

The present inventors have found that human ESCs can be forced to differentiate to neurons by local delivery of the sonic hedgehog agonist purmorphamine (Pur) and retinoic acid (RA) from mesoporous nanoparticles. This approach may therefore be useful for improving initial survival of transplanted stem cells, as well as for achieving desired differentiation of these cells and maintain their long term viability.

According to one aspect, the present invention provides a method of enhancing cell-survival during implantation of stem cells.

According to one embodiment, said method relates to enhancement of the survival of implanted stem cells during and after their differentiation from stem cells to fully functional cells for replacing lost of non-functional host cells. Said enhancement may be achieved by one of the following ways:

a) delivery from mesoporous silica of survival and differentiation factors specific for implanted stem cells and the desired derivatives, b) delivery from mesoporous silica of survival and differentiation factors specific for co-implanted neural crest stem cells and their desired derivatives which are aimed to provide trophic support and functional reinnervation of stem cells used for cell replacement therapy.

According to another aspect of the invention, the above-mentioned method of enhancing cell-survival of stem cells during implantation may also be used as a therapeutic method for treating patients with disorders for which cell replacement therapy is required. Said treatment may be achieved by one of the following ways:

c) by transplanting ESCs/iPSCs or other stem cells, producing desired progenitor cells either before or after transplantation to patients with disorders in which cells are permanently lost or non-functional.

d) by transplanting ECSs/iPSCs, producing desired cells either before or after transplantation to patients with disorders in which cells are permanently lost or non-functional together with neural crest stem cells. Said therapeutic method has the potential to produce neurotrophic support and specific innervation from the differentiated bNCSCs of newly differentiated replaced cells.

According to a further aspect of the invention, the therapeutic method may be directed to patients requiring organs and tissues to be reinnervated after transplantation (cardiac transplants, pancreatic islet transplants, liver transplants etc.) or newly created organs/tissues from stem/progenitor cells of different sources, including somatic cell nuclear transfer, single cell embryo biopsy, arrested embryos, altered nuclear transfer and reprogramming somatic cells. Said method comprises using mesoporous silica for delivery of survival and differentiation factors for:

e) transplanted stem cells, f) in vitro pre-differentiated stem/progenitor cells for sensory neuron subtypes or autonomic neuron subtypes, or glial cell subtypes, g) for co-transplanted neural crest stem cells.

According to yet another aspect, the present invention relates to kits for use with the above-mentioned therapeutic methods.

According to one embodiment, the kit is devised for co-implantation of stem cells with mesoporous silica containing controlled delivery of survival and differentiation factors for the generation of desired type of cells for cell replacement therapy. These cells include, but are not limited to:

i) cardiomyocytes,
ii) skeletal muscle cells,
iii) insulin producing beta-cells,
iv) retinal photoreceptors,
v) midbrain dopaminergic neurons,
vi) spinal motorneurons,
vii) glutamatergic neurons
viii) GAB Aergic neurons
ix) oligodendrocytes
x) astrocytes According to another embodiment, the kit is devised, for example, for a method of reinnervation and trophic support of organs after transplantation or organs/tissues either created from stem/progenitor cells of different sources, or transplanted from organ/tissue donors.

Said kit comprises, in addition to stem cells, one or more of the following cell types in combination with mesoporous silica containing survival and differentiation factors for:

xi) co-transplanted neural crest stem cells,
xii) in vitro pre-differentiated stem/progenitor cells for sensory neuron subtypes or autonomic neuron subtypes, or glial cell subtypes.

The above methods and kits may alternatively comprise cells derived from animals, as these methods and kits may be used for the corresponding veterinary purposes.

The present invention relates also to a pharmaceutical active ingredient for cell differentiation to alleviate cell and cell-related deficiencies in mammals which comprises porous silica containing releasable agents capable of contributing to a cell environment conducive for stem cell differentiation in co-implanted stem cells and/or in endogenous stem cells.

Preferably said porous silica is characterized by a surface area higher than 200 $m^2/g$ and a pore size between 1.5-50 nm.

According to a preferred embodiment, the porous silica particle have a particle shape comprising of spheres, or rod-shaped particles. The porous silica has preferably average particle size and/or sizes in the range between 50-5000 nm and more preferably it is in the form of substantially spherical particles having a size range of 200-500 nm.

In the active ingredient of the invention the releasable agent capable of contributing to a cell environment conducive for stem cell differentiation in co-implanted stem cells and/or in endogenous stem cells is preferably 1-60% of the total weight of the pharmaceutical active ingredient containing silica, and more preferably between 10-45 wt %.

Further, the present invention relates to a pharmaceutical active ingredient for elimination of undifferentiated co-implanted stem cells with the potential for tumor formation in a mammal, comprising in vitro produced porous silica containing releasable agents capable of forcing co-implanted cells to become postmitotic.

Preferably, the in vitro produced porous silica has the above-mentioned chracteristics in terms of surface area and porosity.

According to a preferred embodiment, the co-implanted stem cells which are combined with mesoporous silica are chosen from the group consisting of regional stem cells, embryonic stem (ES) cells, neural crest stem cells, neural stem cells from brain and spinal cord, mesenchymal stem cells, endothelial stem cells, endodermal stem cells, induced pluripotent stem (iPS) cells.

Preferably, the releasable agent(s) are selected from the group consisting of secreted growth factors and morphogens, including, but not limited to fibroblast growth factors (FGFs), Wnts, transforming growth factor (TGF)—beta family members, Hedgehog (hh) proteins, retinoic acid, vascular endothelial growth factor (VEGF), Dickkopf (Dkk)-1, insulin, Activin, SDF-1/CXCL12), pleiotrophin (PTN), insulin-like growth factor 2 (IGF2), ephrin B1 (EFNB1), and cAMP.

The present invention relates also to a delivery system for delivery of a pharmaceutical active ingredient in mammals, comprising a pharmaceutical active ingredient for cell differentiation to alleviate cell and cell-related deficiencies in mammals, said pharmaceutical active ingredient comprising porous silica containing a releasable agent capable of contributing to a cell environment conducive for stem cell differentiation in co-implanted stem cells and/or in endogenous stem cells, and stem cells.

Preferably, said cells are selected from the group consisting of regional stem cells, embryonic (ES) stem cells, neural crest stem cells, neural stem cells from brain and spinal cord, mesenchymal stem cells, endothelial stem cells, endodermal stem cells, iPS cells.

Examples of releasable agents include, but are not limited to, secreted growth factors and morphogens, including, but not limited to, fibroblast growth factors (FGFs), Wnts, transforming growth factor (TGF)—beta family members, and Hedgehog (hh) proteins, retinoic acid, VEGF, Dkk1, insulin, Activin, SDF-1/CXCL12), pleiotrophin (PTN), insulin-like growth factor 2 (IGF2), and ephrin B1 (EFNB1), cAMP

BRIEF DESCRIPTION OF THE SEVERAL VIEWS OF THE DRAWINGS

In the drawings:

FIG. 3A shows how bTUB expressed in some GFP-expressing hESCs;

FIG. 3B shows how HB9 expressed in some GFP-expressing cells;

FIG. 4A shows eGFP-expressing NCSC neurospheres cultured with AMS particles;

FIG. 4B shows faze-contrast pictures of FIG. 4A;

FIG. 4C shows eGFP-expressing NCSC neurospheres cultured without AMS particles;

FIG. 4D shows faze-contrast pictures of FIG. 4C;

FIG. 5A(i) shows in vitro differentiation assay of bNCSCs cultured without special treatment;

FIG. 5A(ii) shows in vitro differentiation assay of bNCSCs cultured with RA;

FIG. 5A(iii) shows in vitro differentiation assay of bNC-SCs cultured with AMS–RA;

FIG. 5B shows the neuro/glial ratio in the RA-treated cultures of FIG. 5A(ii);

FIG. 7A shows a kidney with NCSCs transplants located in a low pole of the kidney;

FIG. 7B shows a kidney where NCSCs migrate towards Islets;

FIG. 7C shows a kidney with reduced migration of NCSCs towards Islets and increased differentiation of NCSCs in the initial location when they were co-transplanted with AMS;

FIGS. 8A(i)-8A(iii) show eGFP-expressing bNCSC under a kidney capsule with migrated bNCSCs towards RFP-expressing pancreatic islets in the other pole of the kidney;

FIG. 8B(i) shows eGFP-expressing bNCSC under a kidney capsule transplanted without AMS;

FIG. 8B(ii) shows eGFP-expressing bNCSC under a kidney capsule co-transplanted with AMS;

DETAILED DESCRIPTION OF THE INVENTION

Figure 1:
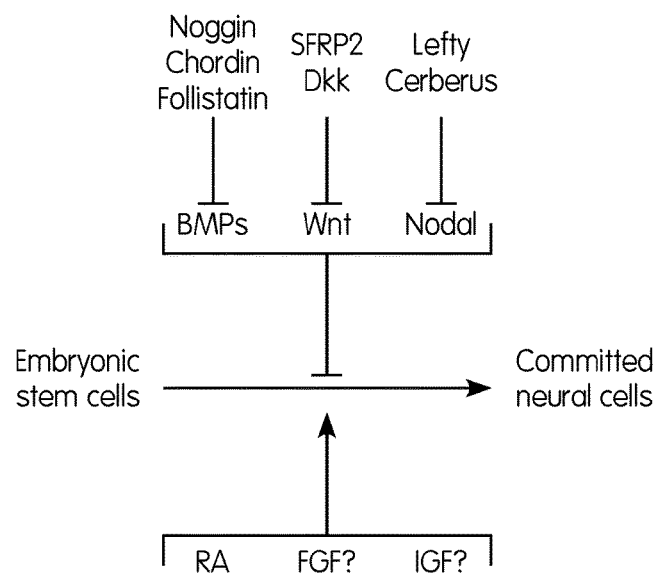
FIG. 1 is a schematic view of in vitro neural induction.

Methods for loading survival and differentiation factors into mesoporous silica The present invention includes a method of loading survival enhancing and differentiation factors into mesoporous particles whereby the porous silica material, be it a solvent extracted or calcined material (see Rambabu Atluri, Niklas Hedin, Alfonso E. Garcia-Bennett. Hydrothermal Phase transformations of cubic mesoporous solid AMS-6. Chemistry of Materials, 2008, 20 (12), 3857-3866.) is mixed with the desired amount of survival enhancing and differentiation factors in a solvent that will dissolve or partially dissolve the aforementioned factors. The mixture may be stirred, centrifuged, spray dried, or filtered after periods between 0.5 hours and 2 days at temperatures between 0-80 degrees Celsius. The recovered solid if the sample is stirred typically contains between 20-49 wt % of factors within the pores of the silica particle, but may contain higher amounts if the loading process is repeated several times.

Sources of Donor Cells for Stem Cell Transplantation

We show the proof-of-principle on the example of ESCs and neural stem cells to differentiate towards neuronal phenotype under effect of extrinsic factors delivered with AMS. However we anticipate that differentiation of different types of cells can be generated from different sources of stem cells with this method. We therefore briefly describe in the following section different sources of stem cells that are considered for cell replacement therapy.

Embryonic stem (ES) cells are capable of generating all cell types in the organism and show great promise for cell replacement therapy in clinical applications. ESCs have been isolated as homogenous cell lines, they can be expanded and modified to meet the needs of the patient using standardized and optimized protocols.

The recent discovery of induced pluripotent stem (iPS) cells offers the possibility to generate patient-specific cells, which can be implanted without ethical or immunological complications. Several laboratories have demonstrated that a limited set of less than four transcription factors is sufficient for dedifferentiation of most somatic cell types to the undifferentiated iPS state (Takahashi K, Yamanaka S. Induction of pluripotent stem cells from mouse embryonic and adult fibroblast cultures by defined factors. Cell 2006; 126: 663-76; Takahashi K, Tanabe K, Ohnuki M, et al. Induction of pluripotent stem cells from adult human fibroblasts by defined factors. Cell 2007; 131:861-72; Huangfu D, Osafune K, Maehr R, et al. Induction of pluripotent stem cells from primary human fibroblasts with only Oct4 and Sox2. Nat Biotechnol 2008; 26:1269-75; Carey B W, Markoulaki S, Hanna J, et al. Reprogramming of murine and human somatic cells using a single polycistronic vector. Proc Natl Acad Sci USA 2009; 106:157-62. Erratum in: Proc Natl Acad Sci USA 2009; 106:5449. Proc Natl Acad Sci USA 2009; 106:11818; Carey B W, Markoulaki S, Beard C, et al. Single-gene transgenic mouse strains for reprogramming adult somatic cells. Nat Methods 2010; 7:56-9; Silva J, Nichols J, Theunissen T W, et al. Nanog is the gateway to the pluripotent ground state. Cell 2009; 138:722-37). The initial protocol of reprogramming adult cells to obtain iPSCs raised concerns of its therapeutic applicability due to the expression of the c-myc proto-oncogene, but newer, improved protocols for iPS cell production show that pluripotency can be achieved without any genetic alteration of the adult cell (Zhou H, Wu S, Joo J Y, et al. Generation of induced pluripotent stem cells using recombinant proteins. Cell Stem Cell 2009; 4:381-4. Erratum in: Cell Stem Cell 2009; 4:581). Recent studies have shown that generation of differentiated cells from iPSCs occurs at a slower rate than for ESCs (Hu B Y, Zhang S C. Directed differentiation of neural-stem cells and subtype-specific neurons from hESCs. Methods Mol Biol 2010; 636:123-37), possibly due to a genetic difference in a developmentally important region of chromosome 12qF1 in the mouse (Stadtfeld M, Apostolou E, Akutsu H, et al. Aberrant silencing of imprinted genes on chromosome 12qF1 in mouse induced pluripotent stem cells. Nature 2010; 465:175-8).

Tissue-specific stem/progenitor cells are attractive source for transplantation since they are already committed to some extent to differentiation towards the desired cell type(s). These cells were found in the human thyroid, with an intrinsic ability to generate thyroidal cells and the potential to produce non-thyroidal cells (Fierabracci A, Puglisi M A, Giuliani L, et al. Identification of an adult stem/progenitor cell-like population in the human thyroid. J Endocrinol 2008; 198:471-87); in the adult human pancreas (Puglisi M A, Guilani L, Fierabracci A 2008 Identification and characterization of a novel expandable adult stem/progenitor cell population in the human exocrine pancreas. J Endocrinol Invest 2008; 31:563-72) in human skeletal muscle (Alessandri G, Pagano S, Bez A, et al. Isolation and culture of human muscle-derived stem cells able to differentiate into myogenic and neurogenic cell lineages. Lancet 2004; 364: 1872-83) human and murine heart (Messina E, De Angelis L, Frati G, et al. Isolation and expansion of adult cardiac stem cells from human and murine heart. Circulation Res 2004; 95:911-21) and human bladder (Fierabracci A, Caione P, Di Giovine M, et al. Identification and characterisation of adult stem/progenitor cells in the human bladder (Bladder spheroids): perspectives of application in pediatric surgery. Ped Surg Int 2007; 23 837-9). However, their potential for regenerative medicine is questionable since these cells are not always easily accessible and they are often poorly viable when obtained from adult tissue.

Mesenchymal stem cells (MSCs) can be easily harvested from e.g. bone marrow, adipose tissue, umbilical cord blood or amnion, are able to differentiate to a variety of mesodermal as well as non-mesodermal cell types in vitro (Franco Lambert A P, Fraga Zandonai A, Bonatto D, et al. Differentiation of human adipose-derived adult stem cells into neuronal tissue: does it work? Differentiation 2009; 77:221-8; Meirelles Lda S, Nardi N B. Methodology, biology and clinical applications of mesenchymal stem cells. Front Biosci 2009; 14:4281-98 09) and can be used for autologous transplantation. MSCs have the ability to modify immune processes (Uccelli A, Moretta L, Pistola V. Mesenchymal stem cells in health and disease. Nat Rev Immunol 2008; 8:726-36; Sadan O, Melamed E, Offen D. Bone-marrow-derived mesenchymal stem cell therapy for neurodegenerative diseases. Expert Opin Biol Ther 2009; 9:1487-97) and were used for transplantation in an undifferentiated state with the intention of promoting tissue repair rather than for the purpose of cell replacement (Kim S U, de Vellis J. Stem cell-based cell therapy in neurological diseases: a review. J Neurosci Res 2009; 87:2183-200; Abdallah B M, Kassem M. The use of mesenchymal (skeletal) stem cells for treatment of degenerative diseases: current status and future perspectives. J Cell Physiol 2009; 218:9-12). MSC transplantation has received considerable attention in the treatment of graft-versus-host disease and showed promising results in clinical trials (Kebriaei P, Isola L, Bahceci E, et al. Adult human mesenchymal stem cells added to corticosteroid therapy for the treatment of acute graft-versus-host disease. Biol Blood Marrow Transplant 2009; 15:804-11; Picinich S C, Mishra P J, Mishra P J, et al. The therapeutic potential of mesenchymal stem cells. Cell- & tissue-based therapy. Expert Opin Biol Ther 2007; 7:965-73).

Current State of Stem Cell Transplantation as Cell Replacement Therapy for Major Disorders There is a long list of medical conditions which are potential therapeutic targets for stem cell transplantation. For some of these disorders no treatment is yet able to significantly change the course of the disease; for others treatment exists, but does not cure the disease or is insufficient. Here we describe disorders with huge impact on the affected individuals and on society, and where treatment is generally thought to benefit strongly in the long run from cell replacement therapy by stem cell transplants. Stem cell transplantation in animal models of these disorders has been and still is the subject of intense research providing evidence, to some degree, of structural repair and functional improvement. Moreover, clinical trials with stem cell transplantation have already been carried out or are in preparation and early results show that this approach is feasible and safe, but therapeutic benefits are so far inconsistent (reviewed in Trounson A. New perspectives in human stem cell therapeutic research. BMC Medicine 2009; 7:2).

1. Myocardial Disease

Ischemic heart disease is the most common cause of death in the Western world. Cardiomyocytes are the contracting elements of the heart and the intrinsic capacity of the heart to replace these cells is very limited. Transplantation of stem cells that can replace lost cardiomyocytes is therefore an attractive option to treat this condition. Cardiomyocytes have been generated in vitro from a wide range of stem/progenitor cells, including iPSCs (Gai H, Leung E L, Costantino P D, et al. Generation and characterization of functional cardiomyocytes using induced pluripotent stem cells derived from human fibroblasts. Cell Biol Int. 2009; 33:1184-93; Kuzmenkin A, Liang H, Xu G, et al. Functional characterization of cardiomyocytes derived from murine induced pluripotent stem cells in vitro. FASEB J 2009; 23:4168-80 Pfannkuche K, Liang H, Hannes T, et al. Cardiac myocytes derived from murine reprogrammed fibroblasts: intact hormonal regulation, cardiac ion channel expression and development of contractility. Cell Physiol Biochem 2009; 24:73-86), ESCs (Beqqali A, van Eldika W, Mummery C, et al. Human stem cells as a model for cardiac differentiation and disease Cell Mol Life Sci 2009; 66:800-13; Steel D, Hyllner J, Sartipy P. Cardiomyocytes derived from human embryonic stem cells—characteristics and utility for drug discovery. Curr Opin Drug Discov Dev 2009; 12:133-40), hematopoietic progenitor/stem cells, MSCs (Choi S C, Shim W J, Lim D S. Specific monitoring of cardiomyogenic and endothelial differentiation by dual promoter-driven reporter systems in bone marrow mesenchymal stem cells. Biotechnol Lett 2008; 30:835-43; Antonitsis P, Ioannidou-Papagiannaki E, Kaidoglou A, et al. Cardiomyogenic potential of human adult bone marrow mesenchymal stem cells in vitro. Thorac Cardiovasc Surg 2008; 56:77-82; Ge D, Liu X, Li L, et al. Chemical and physical stimuli induce cardiomyocyte differentiation from stem cells. Biochem Biophys Res Commun 2009; 381:317-21; Gwak S J, Bhang S H, Yang H S, et al. In vitro cardiomyogenic differentiation of adipose-derived stromal cells using transforming growth factor-beta1. Cell Biochem Funct 2009; 27:148-54), and cardiomyocyte progenitor cells (Smits A M, van Vliet P, Metz C H, et al. Human cardiomyocyte progenitor cells differentiate into functional mature cardiomyocytes: an in vitro model for studying human cardiac physiology and pathophysiology. Nat Protoc 2009; 4:232-43).

An additional source for repair of myocardial contractility are skeletal myoblasts (Nomura T, Ueyama T, Ashihara E, et al. Skeletal muscle-derived progenitors capable of differentiating into cardiomyocytes proliferate through myostatin-independent TGF-beta family signaling. Biochem Biophys Res Commun 2008; 365:863-9), although they do not seem to be able to differentiate to cardiomyocytes (Reinecke H, Poppa V, Murry C E. Skeletal muscle stem cells do not transdifferentiate into cardiomyocytes after cardiac grafting. J Mol Cell Cardiol 2002; 34:241-9; Leobon B, Garcin I, Menasche P, et al. Myoblasts transplanted into rat infarcted myocardium are functionally isolated from their host. Proc Natl Acad Sci USA 2003; 100:7808-11). Intravascular delivery or cardiac transplants of multipotent or pre-differentiated cardiogenic cells from these stem cell sources have been shown to promote cardiac structural repair and functional restoration in animal models of myocardial injury (Fukushima S, Coppen S R, Lee J, et al. Choice of cell-delivery route for skeletal myoblast transplantation for treating post-infarction chronic heart failure in rat. PLoS One 2008; 3:e3071; Hendry S L 2nd, van der Bogt K E, Sheikh A Y, et al. Multimodal evaluation of in vivo magnetic resonance imaging of myocardial restoration by mouse embryonic stem cells. J Thorac Cardiovasc Surg 2008; 136:1028-37; Matsuura K, Honda A, Nagai T, et al. Transplantation of cardiac progenitor cells ameliorates cardiac dysfunction after myocardial infarction in mice. J Clin Invest 2009; 119:2204-17; Jin J, Jeong S I, Shin Y M, et al. Transplantation of mesenchymal stem cells within a poly(lactide-co-epsilon-caprolactone) scaffold improves cardiac function in a rat myocardial infarction model. Eur J Heart Fail 2009; 11:147-53; Okura H, Matsuyama A, Lee C M, et al. Cardiomyoblast-like cells differentiated from human adipose tissue-derived mesenchymal stem cells improve left ventricular dysfunction and survival in a rat myocardial infarction model. Tissue Eng Part C Methods 2010; 16:417-25).

The encouraging results from this experimental research have prompted several clinical trials in patients with myocardial disease, using different types of progenitor/stem cells (Segers V F, Lee R T. Stem-cell therapy for cardiac disease. Nature 2008; 451:937-42; Joggerst S J, Hatzopoulos A K Stem cell therapy for cardiac repair: benefits and barriers. Exp Rev Molec Med Epub 2009 Jul. 8; 11:e20; Piepoli M F. Transplantation of progenitor cells and regeneration of damaged myocardium: more facts or doubts? Insights from experimental and clinical studies. J Cardiovasc Med 2009; 10:624-34).

Protocol for Cardiomyocytes

Cardiomyocyte progenitors were generated from hESC embryoid bodies treated with Activin A, BMP4 or with those 2+ Wnt3 and bFGF. The progenitors express Nkx2.5, Tbx5/20, Gata-4, Mef2c and Hand1/2. Their differentiation to functional cardiomyocytes in vitro can be promoted with VEGF and Dkk1 (Vidarsson H, Hyllner J, Sartipy P. Differentiation of human embryonic stem cells to cardiomyocytes for in vitro and in vivo applications. Stem Cell Rev 2010; 6:108-20).

2. Skeletal Muscle Disorders

Muscular dystrophies include a large number of inherited disorders characterized by severe and progressive degeneration of skeletal muscle fibers, resulting in serious disability and often early death. In view of the genetic basis of this disorder, transplantation of stem cells which are able to form functional muscle fibers is an attractive approach to cure these disorders. Myotubes formation can be achieved from regional stem cells (muscle satellite cells) by activation of transcription factor Pax7 under the influence of FGF and HGF, followed by transcription factors MyoD and MyoG (Yablonka-Reuveni Z, Day K, Vine A, et al. Defining the transcriptional signature of skeletal muscle stem cells. J Anim Sci 2008; 86(14 Suppl):E207-16). Retinoic acid appears to play a critical role in the generation of muscle progenitor stage by activating beta-catenin and inhibiting BMP (Kennedy K A, Porter T, Mehta V et al. Retinoic acid enhances skeletal muscle progenitor formation and bypasses inhibition by bone morphogenetic protein 4 but not dominant negative beta-catenin. BMC Biol 2009; 7:67).

Embryonic stem cells (human, mouse), bone marrow-associated stem cells (human, mouse), stem cells from the hematopoetic or vascular system (human, mouse), adipose tissue derived stem cells (human) and skeletal muscle-associated precursor cells (human, mouse) have been delivered intramuscularly (mostly) or intravascularly to mouse models of muscular dystrophies (Darabi R, Perlingeiro R C. Lineage-specific reprogramming as a strategy for cell therapy. Cell Cycle 2008; 7:1732-7; Quattrocelli M, Cassano M, Crippa S et al. Cell therapy strategies and improvements for muscular dystrophy. Cell Death Differ. 2009 Oct. 30 [Epub ahead of print]). Promising results have been obtained with several, but not all of these approaches. Important limiting factors include extensive early death of grafted cells, failure of grafted cells to differentiate properly and integrate functionally with host muscle tissue. Several clinical trials have been undertaken with transplantation of myogenic stem cells, but with limited success (Tedesco F S, Dellavalle A, Diaz-Manera J et al. Repairing skeletal muscle: regenerative potential of skeletal muscle stem cells. J Clin Invest 2010; 120:11-9). Results from recent experimental studies using ESCs are promising in terms of survival and potential for functional improvement in mouse muscular dystrophy models (Darabi R, Gehlbach K, Bachoo R M, et al. Functional skeletal muscle regeneration from differentiating embryonic stem cells. Nat Med 2008; 14:134-43; Darabi R, Baik J, Clee M, et al. Engraftment of embryonic stem cell-derived myogenic progenitors in a dominant model of muscular dystrophy. Exp Neurol 2009; 220:212-6).

Transplantation of stem cells for repair of dysfunctional muscle have been tried with some success in patients with stress urinary incontinence, a common disorder characterized by reduced tone in pelvic muscle regulation bladder emptying (Nikolaysky D, Chancellor M B. Stem cell therapy for stress urinary incontinence. Neurourol Urodyn 2010; 29 Suppl 1:S36-41).

Protocol for Skeletal Muscle Fibers

Mesodermal progenitors able to generate muscle fibers express Pax3 and Pax 7. Pax3 acts as a master regulator to determine a myogenic lineage (Darabi R, Gehlbach K, Bachoo R M, et al. Functional skeletal muscle regeneration from differentiating embryonic stem cells. Nat Med 2008; 14:134-43; Darabi R, Santos F N, Perlingeiro R C. The therapeutic potential of embryonic and adult stem cells for skeletal muscle regeneration. Stem Cell Rev 2008; 4:217-25). An essential target for Pax3 appears to be FGF signaling through FRGR4 (Lagha M, Kormish J D, Rocancourt D, et al. Pax3 regulation of FGF signaling affects the progression of embryonic progenitor cells into the myogenic program. Genes Dev 2008; 22:1828-37; Lagha M, Sato T, Bajard L, et al. Regulation of skeletal muscle stem cell behavior by Pax3 and Pax7. Cold Spring Harb Symp Quant Biol 2008; 73:307-15) by FGF8, which in combination with Shh promote expression of myogenic regulatory factors (MRFs) myf5 and myoD (Hammond C L, Hinits Y, Osborn D P et al. Signals and myogenic regulatory factors restrict pax3 and pax7 expression to dermomyotome-like tissue in zebrafish. Dev Biol 2007; 302:504-21). Skeletal muscle fibers were also generated from hESCs via generation of multipotent mesenchymal stem cells (Stavropoulos M E, Mengarelli I, Barberi T. Differentiation of multipotent mesenchymal precursors and skeletal myoblasts from human embryonic stem cells. Curr Protoc Stem Cell Biol 2009; Chapter 1:Unit 1F.8). Embryonic skeletal muscle cells express NCAM and are FACS sorted after incubation with anti-NCAM. Sorted cells differentiate to spontaneously twitching muscle cells in vitro and long-term survival after transplantation to mice with toxin-induced muscle damage. No functional data are presented. Retinoic acid appears to play a critical role in the generation of muscle progenitors by activating beta-catenin and inhibiting BMP (Kennedy K A, Porter T, Mehta V et al. Retinoic acid enhances skeletal muscle progenitor formation and bypasses inhibition by bone morphogenetic protein 4 but not dominant negative beta-catenin. BMC Biol 2009; 7:67).

3. Insulin Producing Beta-Cells

Type 1 diabetes is characterized by an autoimmune mediated loss of insulin producing β-cells in the pancreatic islets of Langerhans. Today, transplantation of either the entire pancreas or of isolated islets has become a treatment of choice for selected patients with diabetes mellitus (Frank A M, Barker C F, Markmann J F Comparison of whole organ pancreas and isolated islet transplantation for type 1 diabetes. Adv Surg 2005; 39:137-63; Ryan E A, Bigam D, Shapiro A M. Current indications for pancreas or islet transplant. Diabetes Obes Metab 2006; 8:1-7). However, long-term results after islet transplantation are disappointing with adequate graft function seen in less than 10% of the patients after five years (Ryan E A, Paty B W, Senior P A, et al. Five-year follow-up after clinical islet transplantation. Diabetes 2005; 54:2060-9).

Furthermore, the number of patients in need of new β-cells far outnumbers the limited access to islet tissue for transplantation. Transplantation of stem cells to replace the lost β-cells is therefore an attractive therapy for long-term treatment of type 1 diabetes and also for some cases of type 2 diabetes. Insulin producing β-cells have been generated from several sources, including ESCs (Baharvand H, Jafary H, Massumi M, et al. Generation of insulin-secreting cells from human embryonic stem cells. Dev Growth Differ 2006; 48:323-32; Schroeder I S, Rolletschek A, Blyszczuk P, et al. Differentiation of mouse embryonic stem cells to insulin-producing cells. Nat Protoc 2006; 1:495-507; Marchand M, Schroeder I S, Markossian S, et al. Mouse E S cells over-expressing the transcription factor NeuroD1 show increased differentiation towards endocrine lineages and insulin-expressing cells. Int J Dev Biol 2009; 53:569-78; Evans-Molina C, Vestermark G L, Mirmira R G. Development of insulin-producing cells from primitive biologic precursors. Curr Opin Organ Transplant 2009; 14:56-63; Van Hoof D, D'Amour K A, German M S. Derivation of insulin-producing cells from human embryonic stem cells. Stem Cell Res 2009; 3:73-87), stem/progenitor cells from the exocrine pancreas (Demeterco C, Hao E, Lee S H, et al. Adult human beta-cell neogenesis? Diabetes Obes Metab 2009; 11 Suppl 4:46-53; Noguchi H, Oishi K, Ueda M, et al. Establishment of mouse pancreatic stem cell line. Cell Transplant 2009; 18:563-71; Mato E, Lucas M, Petriz J, et al. Identification of a pancreatic stellate cell population with properties of progenitor cells: new role for stellate cells in the pancreas. Biochem J 2009; 421:181-91), biliary ducts (Nagaya M, Kubota S, Isogai A, et al. Ductular cell proliferation in islet cell neogenesis induced by incomplete ligation of the pancreatic duct in dogs. Surg Today 2004; 34:586-92), MSCs from various sources (Parekh V S, Joglekar M V, Hardikar A A. Differentiation of human umbilical cord blood-derived mononuclear cells to endocrine pancreatic lineage. Differentiation 2009; 78:232-40; Xie Q P, Huang H, Xu B, et al. Human bone marrow mesenchymal stem cells differentiate into insulin-producing cells upon microenvironmental manipulation in vitro. Differentiation 2009; 77:483-91; Kajiyama H, Hamazaki T S, Tokuhara M, et al. Pdx1-transfected adipose tissue-derived stem cells differentiate into insulin-producing cells in vivo and reduce hyperglycemia in diabetic mice. Int J Dev Biol 2009; 54:699-705), from iPSCs derived from fibroblasts of patients with diabetes type 1 (Maehr R, Chen S, Snitow M, et al. Generation of pluripotent stem cells from patients with type 1 diabetes. Proc Natl Acad Sci USA 2009; 106:15768-73). Human ESCs have been converted to beta-cells capable of synthesizing insulin through a stepwise procedure of transcriptional regulation that mimics the normal development of beta-cells (D'Amour K A, Agulnick A D, Eliazer S, et al. Efficient differentiation of human embryonic stem cells to definitive endoderm. Nat Biotechnol. 2005; 23:1534-41; D'Amour K A, Bang A G, Eliazer S, et al. Production of pancreatic hormone-expressing endocrine cells from human embryonic stem cells. Nat Biotechnol 2006; 24:1392-401). Exocrine pancreatic cells were also shown to give rise to insulin producing β-cells by transcriptional reprogramming with a specific combination of the three transcription factors Ngn3 (also known as Neurog3), Pdx1 and Mafa (Zhou Q, Brown J, Kanarek A, et al. In vivo reprogramming of adult pancreatic exocrine cells to beta-cells. Nature 2008; 455: 627-32).

Transplantation of ESCs to diabetic mice also improved glucose homeostasis indirectly by promoting endogenous β-cell neogenesis (Kodama M, Takeshita F, Kanegasaki S, et al. Pancreatic endocrine and exocrine cell ontogeny from renal capsule transplanted embryonic stem cells in streptozocin-injured mice. J Histochem Cytochem 2008; 56:33-44). Human ESCs pre-differentiated to committed pancreatic endoderm developed into functional beta-cells after transplantation to immune-compromised mice (Kroon E, Martinson L A, Kadoya K, et al. Pancreatic endoderm derived from human embryonic stem cells generates glucose-responsive insulin-secreting cells in vivo. Nat Biotechnol 2008; 26:443-52). Interestingly, treatment of the recipients with the beta-cell toxin streptozotocin destroyed their endogenous beta-cell population, but the grafted cells were protected and provided a functional source of insulin. Thus, although efficient and reproducible replacement of lost β-cells in type 1 diabetes have still not been fully achieved with stem cell transplants (reviewed in Trounson A. New perspectives in human stem cell therapeutic research. BMC Medicine 2009; 7:2), promising steps in this direction have been taken.

Protocol for Beta-Cells

Protocol for generating insulin producing beta-cells from hESCs involve stepwise lineage restriction generating in sequence: definitive endodermal cells (Activin+Wnt3), primitive foregut endoderm (FGF10+KAAD-cyclopamine), posterior foregut endoderm (RA+FGF10+KAAD-cyclopamine), pancreatic endoderm and endocrine precursors (Extendin-4), and hormone producing cells (IGF1+HGF). Transcription factor profiles are: Sox17, CER, FoxA2, and the cytokine receptor CXCR4 (definitive endodermal cells), Hnf1B, Hnf4A (primitive foregut endoderm), Pdx1, Hnf6, H1xB9 (posterior foregut endoderm), Nkx6.1, Nkx2.2, Ngn3, Pax4 (pancreatic endoderm and endocrine precursors). (D'Amour K A, Bang A G, Eliazer S, et al. Production of pancreatic hormone-expressing endocrine cells from human embryonic stem cells. Nat Biotechnol 2006; 24:1392-401; Kroon E, Martinson L A, Kadoya K, et al. Pancreatic endoderm derived from human embryonic stem cells generates glucose-responsive insulin-secreting cells in vivo. Nat Biotechnol 2008; 26:443-52).

An improved protocol has been suggested which focuses on regulating the key signaling pathways form ESC to insulin producing beta-cells (Champeris Tsaniras S, Jones P M. Generating pancreatic beta-cells from embryonic stem cells by manipulating signaling pathways. J Endocrinol. 2010 Apr. 12. [Epub ahead of print]). According to this protocol the principles are: mesendoderm (stimulating Wnt and nodal pathways, down-regulating phosphatidylinositol 3-kinase pathway (PI3K)), definitive endoderm (remove Wnt), posterior foregut (down-regulate Wnt), pancreatic endoderm (block Shh), beta-cell precursors (block Notch), beta-cells (block PI3K, stimulate Shh).

4. Retinal Disease

Age-related macular degeneration is associated with the loss of photoreceptors and a common cause of blindness or severe visual impairment in the aging Western population. Efficient treatment for this disorder is currently lacking. Stem cells have been identified and characterized in several locations of the adult mammalian eye, as well as the molecular pathways leading to their differentiation to different cell types (Locker M, Borday C, Perron M. Stemness or not stemness? Current status and perspectives of adult retinal stem cells. Curr Stem Cell Res Ther 2009; 4:118-30). However, recruiting these cells in vivo to replace lost photoreceptors has so far been unsuccessful. On the other hand, photoreceptors or retinal ganglion cells have been generated from iPSCs, ESCs and retinal stem/progenitor cells in vitro (Mayer E J, Carter D A, Ren Y et al. Neural progenitor cells from postmortem adult human retina. Br J Ophthalmol 2005; 89:102-6; Zhao B, Allinson S L, Ma A et al. Targeted cornea limbal stem/progenitor cell transfection in an organ culture model. Invest Ophthalmol Vis Sci 2008; 49:3395-40; Hirami Y, Osakada F, Takahashi K et al. Generation of retinal cells from mouse and human induced pluripotent stem cells. Neurosci Lett 2009; 458:126-31; Osakada F, Jin Z B, Hirami Y et al. In vitro differentiation of retinal cells from human pluripotent stem cells by small-molecule induction. J Cell Sci 2009; 122(Pt 17):3169-79). Following transplantation, these cells are able to integrate into the retinal network, differentiate to functional photoreceptors and help preserve or restore visual function in experimental model of retinal degeneration (Klassen H. Transplantation of cultured progenitor cells to the mammalian retina. Expert Opin Biol Ther 2006; 6:443-51; Klassen H, Schwartz P H, Ziaeian B et al. Neural precursors isolated from the developing cat brain show retinal integration following transplantation to the retina of the dystrophic cat. Vet Ophthalmol 2007; 10:245-53; Gias C, Jones M, Keegan D et al. Preservation of visual cortical function following retinal pigment epithelium transplantation in the RCS rat using optical imaging techniques. Eur J Neurosci 2007; 25:1940-8 Pinilla I, Cuenca N, Sauvé Y et al. Preservation of outer retina and its synaptic connectivity following sub-retinal injections of human RPE cells in the Royal College of Surgeons rat. Exp Eye Res 2007; 85:381-92; Wang S, Girman S, Lu B et al. Long-term vision rescue by human neural progenitors in a rat model of photoreceptor degeneration. Invest Ophthalmol Vis Sci 2008; 49:3201-6; Chen F K, Uppal G S, MacLaren R E et al. Long-term visual and microperimetry outcomes following autologous retinal pigment epithelium choroid graft for neovascular age-related macular degeneration. Clin Exp Ophthalmol 2009; 37:275-85). Results from preclinical studies have verified the safety of these protocols Francis P J, Wang S, Zhang Y et al. Subretinal transplantation of forebrain progenitor cells in nonhuman primates: survival and intact retinal function. Invest Ophthalmol Vis Sci 2009; 50:3425-31; Lu B, Malcuit C, Wang S et al. Long-term safety and function of RPE from human embryonic stem cells in preclinical models of macular degeneration. Stem Cells 2009; 27:2126-35) and clinical trials in patients with age-related macular degeneration are in preparations (Coffey P. Interview: stemming vision loss with stem cells: seeing is believing. Regen Med 2009; 4:505-7). The experimental basis for successful clinical trials is thus promising. However, tools to optimize survival and differentiation of stem/progenitor transplants when they hosted by retinal tissue undergoing a chronic degenerative process, might still be needed.

Protocol for Retinals Cells

Various types of retinal cells were generated from hESCs (Lamba D A, Karl M O, Ware C B, et al. Efficient generation of retinal progenitor cells from human embryonic stem cells. Proc Natl Acad Sci USA 2006; 103:12769-74; Reh T A, Lamba D, Gust J. Directing human embryonic stem cells to a retinal fate. Methods Mol Biol 2010; 636:139-53). Embryoid bodies were produced and thereafter treated with IGF1, Noggin (BMP inhibitor) and Dkk1 (Wnt inhibitor). This forces hESCs to adopt a retinal progenitor phenotype, expressing Pax6 and Chx10. Exposing these progenitors to N—(N-(3,5-difluorophenacetyl)-1-alanyl)-S-phenylglycine t-butyl ester (DAPT), a blocker of Notch signaling, the progenitor cells will undergo neuronal differentiation). A similar protocol was used to generate retinal cells from human iPSCs (Lamba D A, McUsic A, Hirata R K, et al. Generation, purification and transplantation of photoreceptors derived from human induced pluripotent stem cells. PLoS One 2010; 5:e8763). Decision to undergo photoreceptor differentiation is under the control of transcription factor Blimp1 (Brzezinski J A 4th, Lamba D A, Reh T A. Blimp1 controls photoreceptor versus bipolar cell fate choice during retinal development. Development 2010; 137:619-29).

5. Parkinson's Disesae

In Parkinson's disease (PD), the dopamine-releasing neurons in the substantia nigra are gradually lost, resulting in the progressive and severely disabling motor dysfunction which is the hallmark of this disease. Previous studies in experimental animal models of PD have shown that dopamine release can be restored and motor dysfunction reversed by transplantation of embryonic neurons into the striatum (Lindvall O, Kokaia Z. Prospects of stem cell therapy for replacing dopamine neurons in Parkinson's disease. Trends Pharmacol Sci 2009; 30:260-8; Lindvall O, Kokaia Z. Stem cells in human neurodegenerative disorders—time for clinical translation? J Clin Invest 2010; 120:29-40). Clinical trials with human embryonic dopaminergic (DA) neurons initially provided encouraging results, but later follow-up evaluations indicate only limited success (Schwarz J. Developmental perspectives on human midbrain-derived neural stem cells. Parkinsonism Relat Disord 2007; 13 Suppl 3:S466-8).

DA neurons have been generated in vitro from iPSCs, ESCs, MSCs and regional stem/progenitor cells. In vitro pre-differentiated cells were subsequently grafted into the striatum and found to partially reverse PD-like symptoms in animal models (Rodríguez-Gómz J A, Lu J Q, Velasco I, et al. Persistent dopamine functions of neurons derived from embryonic stem cells in a rodent model of Parkinson disease. Stem Cells 2007; 25:918-28; Cho M S, Lee Y E, Kim J Y, et al. Highly efficient and large-scale generation of functional dopamine neurons from human embryonic stem cells. Proc Natl Acad Sci USA 2008; 105:3392-7; Parish C L, Castelo-Branco G, Rawal N, et al. Wnt5a-treated midbrain neural stem cells improve dopamine cell replacement therapy in parkinsonian mice. J Clin Invest 2008; 118:149-60; Sanchez-Pernaute R, Lee H, Patterson M, et al. Parthenogenetic dopamine neurons from primate embryonic stem cells restore function in experimental Parkinson's disease. Brain 2008; 131(Pt8):2127-39). However, the mechanism(s) responsible for symptom reversal are not fully understood, since functional improvement in an animal model of PD was shown to occur from human neural progenitor cell transplants without differentiation to DA neurons (Hovakimyan M, Haas S J, Schmitt O, et al. Mesencephalic human neural progenitor cells transplanted into the adult hemiparkinsonian rat striatum lack dopaminergic differentiation but improve motor behaviour. Cells Tissues Organs 2008; 188:373-83). Encouraging results in an animal model of PK were recently reported with striatal transplants of ESCs, which gave rise to an abundance of functional DA neurons after forced expression of the TF Lmx1a (Friling S, Andersson E, Thompson L H, et al. Efficient production of mesencephalic dopamine neurons by Lmxla expression in embryonic stem cells. Proc Natl Acad Sci USA 2009; 106:7613-8).

Protocol for Dopaminergic Neurons

Protocol for ESC differentiation to DA neurons include overexpression of the transcription factor Nurr1 followed by their exposure to Shh, FGF-8 and ascorbic acid (Lee S H, Lumelsky N, Studer L, Auerbach J M, McKay R D. Efficient generation of midbrain and hindbrain neurons from mouse embryonic stem cells. Nat Biotechnol. 2000 June; 18(6):675-9; Kriks S, Studer L. Protocols for generating ES cell-derived dopamine neurons. Adv Exp Med Biol. 2009; 651:101-11; Lindvall O, Kokaia Z. Prospects of stem cell therapy for replacing dopamine neurons in Parkinson's disease. Trends Pharmacol Sci. 2009 May; 30(5):260-7.). Alternatively to the combination of stromal cell-derived factor 1 (SDF-1/CXCL12), pleiotrophin (PTN), insulin-like growth factor 2 (IGF2), and ephrin B1 (EFNB1). This combination applied to hESCs induces their differentiation to TH-positive neurons in vitro, expressing midbrain specific markers, including Engrailed 1, Nurr1, Pitx3, and dopamine transporter (DAT), and capable of generating action potentials and forming functional synaptic connections (Vazin T, Becker K G, Chen J, et al. A novel combination of factors, termed SPIE, which promotes dopaminergic neuron differentiation from human embryonic stem cells. PLoS One 2009; 4:e6606).

6. Motor Neuron Disease

Amyotrophic lateral sclerosis (ALS), spinal bulbar muscular atrophy (or Kennedy's disease), spinal muscular atrophy (SMA) and spinal muscular atrophy with respiratory distress 1 are neurodegenerative disorders leading to loss of motor neurons and death of the patient. There is currently no treatment that can significantly halt or delay the disease progression. The pathogenesis of these disorders are incompletely known, but compromised function in surrounding astrocytes and/or microglia have been implicated. Stem cell based therapy with replacement of lost motor neurons as well as of replacement of dysfunctional astrocytes is therefore considered (Mazzini L, Vercelli A, Ferrero I, Mareschi K, Boido M, Servo S, Oggioni G D, Testa L, Monaco F, Fagioli F. Stem cells in amyotrophic lateral sclerosis: state of the art. Expert Opin Biol Ther. 2009 October; 9(10):1245-58; Papadeas S T, Maragakis N J. Advances in stem cell research for Amyotrophic Lateral Sclerosis. Curr Opin Biotechnol. 2009 October; 20(5):545-51. Epub 2009 Oct. 12.Review. PubMed PMID: 19819686.). For disorders such as ALS which only affects adults, the possibility to restore lost neuromuscular connections by motor neuron replacement is problematic given the long distances from the spinal cord to the target muscles. Using stem cells to generate astrocytes for neuroprotection may therefore be the most rational approach in this disorder. However, for SMA, which affects infants or children, replacing lost motor neurons is an attractive strategy.

Protocol for Motor Neurons

Motor neurons were generated from human ESCs using neural differentiation medium, treatment with RA (Pax6 expressing primitive neuroepithelial cells), RA+Shh (Pax6/Sox1 expressing neuroepithelial cells, which gradually start to express the motor neuron progenitor marker Olig2). Reducing RA+Shh concentration promotes the emergence of motor neurons expressing HB9 and Islet1. The addition of brain-derived neurotrophic factor (BDNF), glial-derived neurotrophic factor (GDNF), insulin-like growth factor-1 (IGF1), and cAMP promotes process outgrowth (Hu B Y, Du Z W, Zhang S C. Differentiation of human oligodendrocytes from pluripotent stem cells. Nat Protoc 2009; 4:1614-22; Hu B Y, Weick J P, Yu J, et al. Neural differentiation of human induced pluripotent stem cells follows developmental principles but with variable potency. Proc Natl Acad Sci USA 2010; 107:4335-40).

7. Stroke, Brain Injury and Spinal Cord Injury

Stroke is a leading cause of lifelong disability and death in the western world. Traumatic brain injury is a leading cause of death and long-term disability in young adults in the western world. Spinal cord injury is less frequent than traumatic brain injury but usually affects young individuals and results in serious disability and reduced quality of life for the patients. Stem cell transplantation is an attractive strategy in all these conditions, both in terms of achieving early neuroprotection, and in restoring lost functions during the rehabilitation phase (Bliss T M, Andres R H, Steinberg G K. Optimizing the success of cell transplantation therapy for stroke. Neurobiol Dis 2010; 37:275-83; Lindvall O, Kokaia Z. Stem cells in human neurodegenerative disorders—time for clinical translation? J Clin Invest 2010; 120:29-40; Orlacchio A, Bernardi G, Orlacchio A, et al. Stem cells: an overview of the current status of therapies for central and peripheral nervous system diseases. Curr Med Chem 2010; 17:595-608; Ronaghi M, Erceg S, Moreno-Manzano V, et al. Challenges of stem cell therapy for spinal cord injury: human embryonic stem cells, endogenous neural stem cells, or induced pluripotent stem cells? Stem Cells 2010; 28:93-9). Thus, the choice of stem cells and desired derivatives may be different depending on the stage of the disorder. The fact that these conditions results in loss of different glial and neuronal cell types presents additional challenges.

For stroke and traumatic brain injury, restoring function in local neural circuitry may be the most relevant. The basic components of these circuitries are glutamatergic and GABAergic neurons, as well as cholinergic neurons for selected circuitry mediating cognitive functions. Glutamatergic neurons also form major parts of the descending motor projection pathways from the cerebral cortex to the brain stem and spinal cord. Implantation of GABAergic neurons have shown promising therapeutic results in experimental models of epilepsy which is a common sequelae of traumatic brain injury.

Spinal cord injuries are often contusion injuries which lead to loss of white matter oligodendrocytes and myelin and hence conduction failure in affected ascending and descending pathways. Restoring myelin competent oligodendrocytes is therefore a prime objective after spinal cord injury. Additional targets for cell replacement in this condition are glutamatergic neurons, which can form descending connections across the lesion site and thereby restore lost motor and autonomic functions below the injury site.

Protocol for Glutamatergic Neurons

Glutamatergic neurons can be generated from mouse ESCs in vitro by producing cell aggregates which are then treated for 8 days with RA. This results in the Pax6 expressing cells radial glial cells, which after additional culturing in N2 followed by "complete" medium results in ca 95% glutamate neurons (Bibel M, Richter J, Lacroix E, et al. Generation of a defined and uniform population of CNS progenitors and neurons from mouse embryonic stem cells. Nat Protoc 2007; 2:1034-43).

Protocol for GABAergic Neurons

GABAergic neurons were generated from mouse ESCs by exposing embryoid bodies (EBs) for 3 days to all-trans-RA. After subsequent culture in serum-free neuronal induction medium, comprising Neurobasal medium supplemented with B27, bFGF and EGF ca 95% GABA neurons developed (Chatzi C, Scott R H, Pu J, et al. Derivation of homogeneous GABAergic neurons from mouse embryonic stem cells. Exp Neurol 2009; 217:407-16).

Protocol for Oligodendrocytes

Oligendrocyte precursors (OPCs) capable of developing to mature myelinating oligodendrocytes were generated from human (h) ESCs (Hu B Y, Du Z W, Zhang S C. Differentiation of human oligodendrocytes from pluripotent stem cells. Nat Protoc 2009; 4:1614-22). hESCs are first directed toward the neuroectoderm fate under a chemically defined condition in the absence of growth factors for 2 weeks and express neuroectoderm transcription factors, including Pax6 and Sox1. Next hESCs are exposed to the caudalizing factor retinoic acid (RA) and the ventralizing morphogen Shh for 10 d to begin expression of Olig2. To prevent the differentiation to motoneurons and promote the generation of OPCs, cells are cultured with we use FGF2 for 10 d. By day 35, the Olig2 progenitors co-express NkxX2.2 and no longer give rise to motoneurons. The co-expression of Olig2 and Nkx2.2 reflects a stage prior to human OPCs ("pre-OPCs). These are finally cultured in a glia medium containing triiodothyronine (T3), neurotrophin 3 (NT3), PDGF, cAMP, IGF-1 and biotin, which individually or synergistically can promote the survival and proliferation of the hESC derived OPCs, for another 8 weeks to generate OPCs. These OPCs are bipolar or multipolar, express Olig2, Nkx2.2, Sox10 and PDGFRα, become motile and are able to differentiate to competent oligodendrocytes.

There is also a simpler protocol for generating OPCs from mouse ESCs (Jiang P, Selvaraj V, Deng W. Differentiation of embryonic stem cells into oligodendrocyte precursors. J Vis Exp. 2010; pii:1960).

EXAMPLES

Example 1: Induced Differentiation of Transplanted Human Embryonic Stem Cells with Shh and Retinoic Acid Delivered with Mesoporous Silica Background: Embryonic stem cells (ESCs) differentiate into motor neurons, establish functional synapses with muscle fibers, and acquire physiological properties characteristic of embryonic motor neurons when cultured with sonic hedgehog (Shh) agonist and retinoic acid (RA) (Wichterle H, Lieberam I, Porter J A, et al. Directed differentiation of embryonic stem cells into motor neurons. Cell 2002; 110:385-97; Miles G B, Yohn D C, Wichterle H, et al. Functional properties of motoneurons derived from mouse embryonic stem cells. J Neurosci 2004; 24:7848-58). ESC-derived motorneurons transplanted into the developing chick neural tube projected axons toward muscles, received synaptic input, and developed electrophysiological properties similar to endogenous motor neurons (Soundararajan P, Miles G B, Rubin L L, et al. Motoneurons derived from embryonic stem cells express transcription factors and develop phenotypes characteristic of medial motor column neurons. J Neurosci 2006; 26:3256-68; De Marco Garcia and Jessel, 2008). These results show that ESCs after Shh and RA treatment readily differentiate to functional motor neurons in vitro and can be subjected to transplantation.

Motor neurons were also generated in vitro by activation of transcription factors (TFs) Olig2 and HB9 in the presence of Shh and RA (Zhang X, Cai J, Klueber K M, Guo Z, et al. Role of transcription factors in motoneuron differentiation of adult human olfactory neuroepithelial-derived progenitors. Stem Cells 2006; 24:434-42). In developmental studies it was shown that Nkx6.1 and Isl1 TFs govern the differentiation of stem cells to motor neurons of the lateral motor column (LMC motor neurons) (De Marco Garcia N V, Jessell T M. Early motor neuron pool identity and muscle nerve trajectory defined by postmitotic restrictions in Nkx6.1 activity. Neuron 2008; 57:217-31), which innervate the muscles of the limbs.

Material and methods: Here we use human (h) ESCs and guide their differentiation to motor neurons in the dorsal root ganglion (DRG) cavity of adult recipient rats by administration of extrinsic factors (Shh agonist and RA delivered with mesoporous nanoparticles). The hESCs in our experiment expressed green fluorescent protein (GFP).

AMS-silica

The mesoporous silica was prepared as previously described (Garcia-Bennett et al., 2008). Loading with RA was performed by adding 250 mg of RA to 500 mg of AMS-6 silica in 20 ml of ethanol and left at room temperature for 30 minutes before filtering and drying as a powder.

The loading with PUR was performed by adding 5 mg of PUR to 500 mg of AMS-6 silica. The loading was performed in a mixture of DMSO/ethanol, and at room temperature. After loading the sample was filtered and washed with H2O, the dried for a short period. To each transplants was added mesoporous silica containing 25 µg of RA and 150 µg of purmorphamine The neurospheres were mixed in the Eppendorf with the nanoparticles and then transplanted to the DRG cavity.

Figures 2A, 2B:
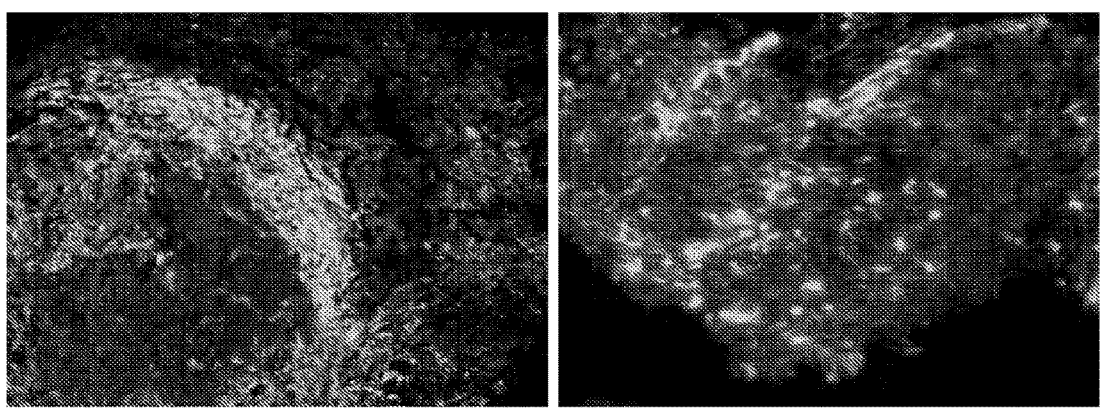
FIG. 2A shows hESC transplants 2 months after transplantation of the DRG cavity to adult nu/nu mice with untreated transplants.
FIG. 2B shows hESC transplants 2 months after transplantation of the DRG cavity to adult nu/nu mice with AMS+RA+Purmorphamine.

Material: After 2 months the mice were perfused via the left ventricle with cold 4% formaldehyde (w/v) and 14% saturated picric acid (v/v) in 0.15M phosphate buffer, post-fixed for 4 hs, and stored overnight in cold phosphate buffer containing 15% sucrose for cryoprotection. 14 µm cryosections were cut and analysed in a Nikon fluorescence microscope. The untreated hESCs showed mixed morphology with typical teratoma formation, whereas treated transplants demonstrated a developed morphology of neuronal cells with extended processes. FIGS. 2A-2B show hESC transplants 2 months after transplantation to the DRG cavity of adult nu/nu mice. FIG. 2A shows untreated transplants, FIG. 2B shows transplants with AMS+RA+Purmorphamine.

The immunostaining confirmed the presence of beta-tubulin (bTUB) positive cells (neuronal marker) in treated transplants and some of the cells expressed HB9 transcription factor—the marker for motor neuronal differentiation (see FIGS. 3A-3B).

FIG. 3A shows how bTUB (indicated with the arrow) is expressed in some GFP-expressing hESCs. FIG. 3B shows how HB9 (indicated with stars) is expressed in some GFP-expressing cells.

We were thus able to induce differentiation of undifferentiated ESCs towards motor neurons in vivo by RA and Shh delivered with mesoporous silica.

Example 2: Differentiation of Neural Crest Stem Cells Toward Neuronal Phenotype In Vitro by RA Delivered with Mesoporous Silica Background: The RA receptor RAR-beta2 is expressed in dorsal root ganglion (DRG) neuron subtypes. It was shown that retinoid signaling has a role in neurite outgrowth in vivo (Corcoran J, Shroot B, Pizzey J, et al. The role of retinoic acid receptors in neurite outgrowth from different populations of embryonic mouse dorsal root ganglia. J. Cell Sci 2000; 113:2567-74; Dmetrichuk J M, Spencer G E, Carlone R L. Retinoic acid-dependent attraction of adult spinal cord axons towards regenerating newt limb blastemas in vitro. Dev Biol 2005; 281:112-20) by demonstrating that in a peripheral nerve crush model there is less sensory neurite outgrowth in RAR-beta null compared to wild-type mice. In vitro experiments identified sonic hedgehog (Shh) as a downstream target of the RAR-beta2 signaling pathway since it is expressed in the injured DRG of wild-type but not RAR-beta null mice and that Shh alone cannot induce neurite outgrowth but potentiates RAR-beta2 signaling in this process (So P L, Yip P K, Bunting S, et al. Interactions between retinoic acid, nerve growth factor and sonic hedgehog signalling pathways in neurite outgrowth. Dev Biol. 2006; 298:167-75). We culture boundary cap neural crest stem cells (bNCSCs) as neurospheres. These cells have the potential produce neurons and glial cells in vitro and can be induced to produce specific type of neurons in vivo by conditional activating of key transcription factors for nociceptor neuron differentiation (Aldskogius H, Berens C, Kanaykina N, et al. Regulation of boundary cap neural crest stem cell differentiation after transplantation. Stem Cells 2009; 27:1592-603).

Material and Methods:

bNCSCs were isolated in a semiclonal fashion from from EGFP embryos on embryonic day (E)11, as described previously (Hjerling-Leffler J, Marmigére F, Heglind M, et al. The boundary cap: a source of neural crest stem cells that generate multiple sensory neuron subtypes. Development 2005; 132:2623-32). Briefly, the DRGs along with boundary caps were mechanically separated from the isolated spinal cord and mechano-enzymatically dissociated using Collagenase/Dispase (1 mg/ml) and DNase (0.5 mg/ml) for 30 minutes at room temperature. Cells were plated at 0.5-1×10$^5$ cells/cm$^2$ in N2 medium containing B27 (Gibco, Grand Island, N.Y., www.invitrogen.com) as well as EGF and basic fibroblast growth factor (R&D Systems, Minneapolis, www.rndsystems.com; 20 ng/ml, respectively). After 12 hours, nonadherent cells were removed together with half of the medium before adding fresh medium. The medium was changed every other day (50% of the medium replaced with fresh medium) until neurospheres could be observed after approximately 2 weeks of culture.

Here we performed differentiation assay of bNCSCs in vitro under three conditions—bNCSC alone, bNCSC+RA and bNCSC+AMS-RA.

Cells were plated at a density of 1.2×10$^3$ cells on a poly-D-lysine (50 µg/ml)/laminin (20 ng/ml)-coated coverslip and maintained in Dulbecco's modified Eagle's medium-F12/neurobasal medium supplemented with N2, B27, 0.1 mM nonessential amino acids and 2 mM sodium pyruvate. To each well were added AMS with 24 ng of RA for 3 days.

After 3 days the cultures were fixed and immunolabeling was performed as described previously (Kozlova E N. Differentiation and migration of astrocytes in the spinal cord following dorsal root injury in the adult rat. Eur J Neurosci 2003; 17:782-90). Primary antibodies were anti-bIII-tubulin (bTUB; mouse monoclonal; Covance, Princeton, N.J., www.covance.com, 1:500; anti-glial fibrillary acidic protein (GFAP; rabbit polyclonal; DAKO, Glostrup, Denmark, www.dako.com; 1:1,000). Secondary antibodies (Jackson Immunoresearch Laboratories, West Grove, Pa., www.jacksonimmuno.com) were diluted in PBS with 0.3% Triton X-100 and 0.1% sodium azide: AMCA-conjugated donkey anti-rabbit and anti-mouse, Cy3-conjugated donkey anti-mouse).

The AMS were added to the cultures and the time-window for their presence before dissolving in the culture medium was established. We also analyzed their contact with the stem cells. After 3 and 7 days the cultures were fixed and processed for immunohistochemistry. After staining 10 photographs were taken from each slide and the ratios of neurons and glial cells were calculated in all types of experiments. We also calculated the neurite length per cell as a measure of the level of neuronal differentiation (Kozlova E N. Differentiation and migration of astrocytes in the spinal cord following dorsal root injury in the adult rat. Eur J Neurosci 2003; 17:782-90).

Results:

We found that AMS have a strong affinity to the stem cells and tightly attach neurospheres during first minutes/hours after placing to the culture dish. The differentiation of neurospheres was not hampered and the cells in spite on their close contact with the particles successfully spread on the surface and differentiated (see FIGS. 4A-4D).

In FIGS. 4A-4D, left columns (FIGS. 4A-4B) show eGFP-expressing NCSCs neurospheres cultured with the AMS particles (the eGFP spheres look perforated. On the faze-contrast pictures the particles are seen as dark threeangles—second column (FIG. 4B)). On the right columns (FIGS. 4C-4D) the NCSCs are cultures without particles. In both cases the spheres differentiated and spread on the surface. The amount of particles reduced during first week. We then compared if RA delivered to the NCSCs will have similar effect on their differentiation compare to RA delivered with AMS (AMS-RA). RA and AMS-RA both induced neuronal differentiation (FIGS. 5A(i)-5A(iii)). Based on the calculation of neurite lengths differentiation of neurons in RA treated cultures increased up to 37% and in AMS-RA treated cultures up to 18% compared to non-treated neurospheres and the neuron/glia ratio in RA-treated cultures increased 3.4 times and in AMS-RA 3.9 times compared to neurospheres-alone (FIG. 5B).

Figure 6A:
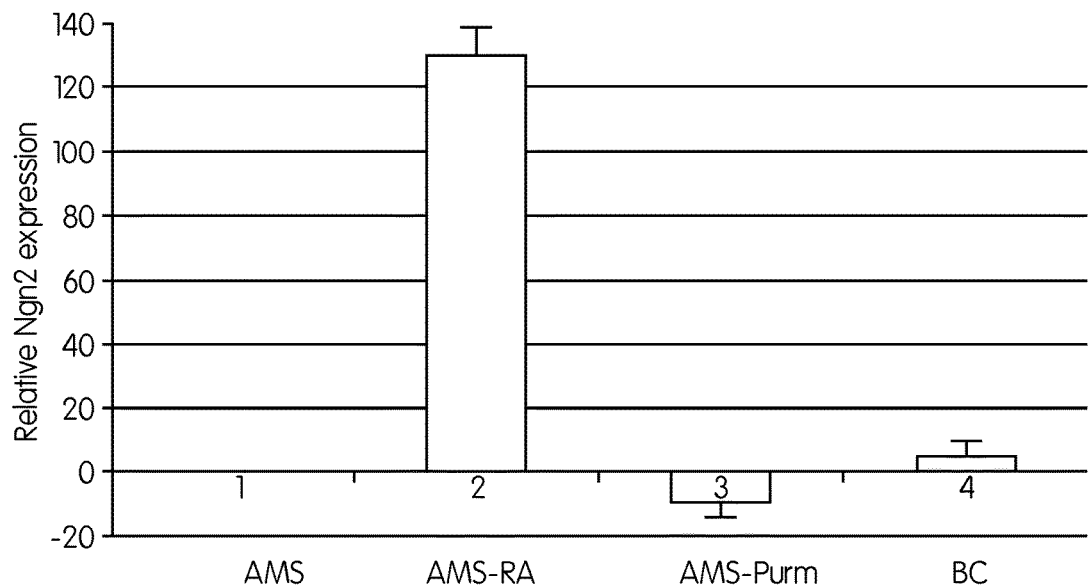
FIG. 6A shows the relative Ngn2 expressions of transcriptions factors in response to activation of RA and Shh of bNCSCs cultured alone, with AMS, with AMS–RA and with AMS-Purm.
Figure 6B:
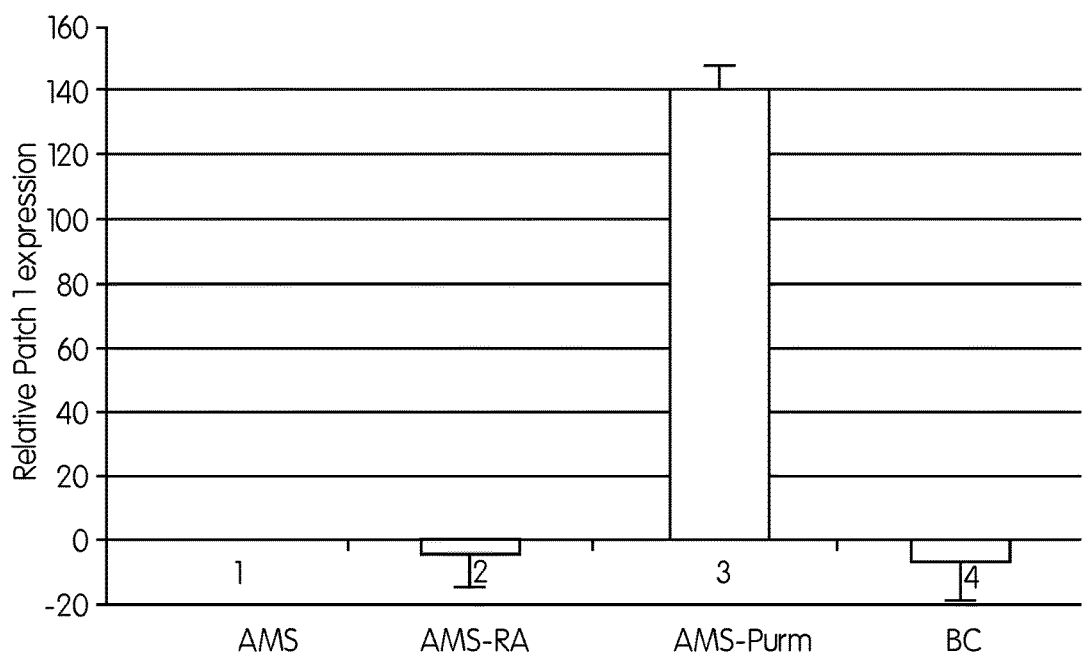
FIG. 6B shows the relative Patch1 expression of transcriptions factors in response to activation of RA and Shh of bNCSCs cultured alone, with AMS, with AMS–RA and with AMS-Purm.
Figure 9A:
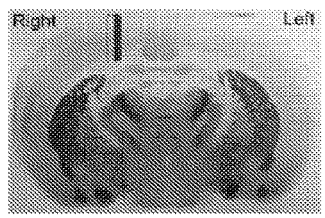
FIG. 9A shows a coronal section of a rat cerebral cortex one week after a focal injury.
Figure 9B:
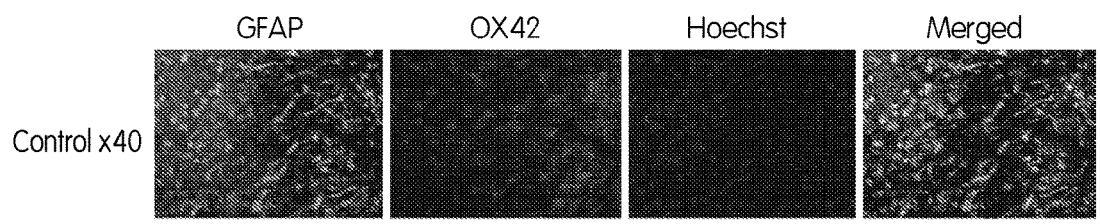
FIG. 9B shows coronal sections through a rat cerebral cortex one week after a focal injury without treatment.
Figure 9C:
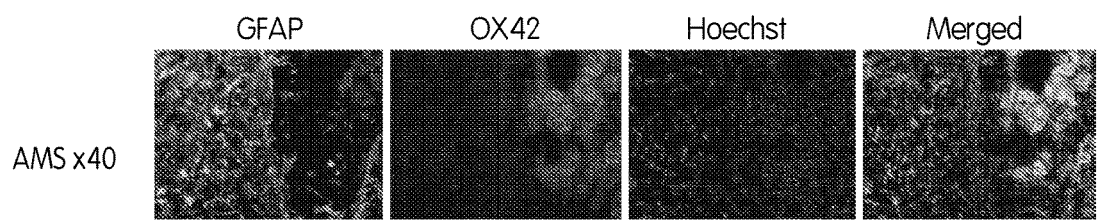
FIG. 9C shows coronal sections through a rat cerebral cortex one week after a focal injury with AMS.
Figure 9D:
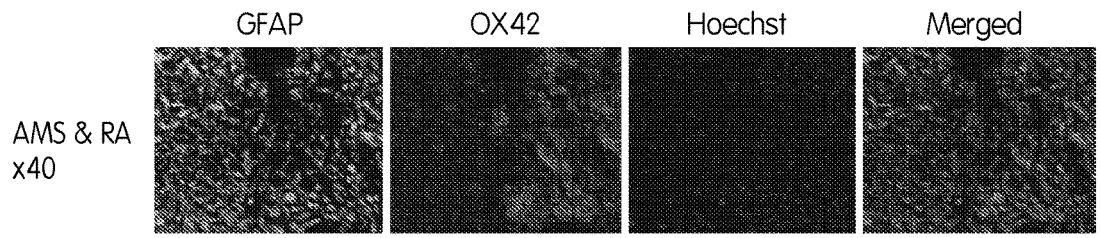
FIG. 9D shows coronal sections through a rat cerebral cortex one week after a focal injury with AMS–RA.

FIGS. 5A(i)-5A(iii) show in vitro differentiation assay of bNCSCs cultured without special treatment (upper panel) (FIG. 5A(i)), with RA (middle panel) (FIG. 5A(ii)) and with AMS-RA (lower panel) (FIG. 5A(iii)). The level of neuronal differentiation in the middle and lower panels is higher compared to the upper panel (untreated cells), whereas differentiation of glial cells is strongly reduced in RA and AMS-RA treated cultures. First column–eGFP(bNCSCs), second column GFAP(glial marker), third column bTUB (neuronal marker). The graph of FIG. 5B shows increased neuro/glial ration in the RA-treated cultures. Furthermore we performed RT-PCR analysis of bNCSCs cultured alone (BC), NCSCs cultures with AMS, with AMS-RA and with AMS-Purm (purmorphomine—the agonist of Shh) and found specific expression of transcription factors in response to activation of RA and Shh (FIGS. 6A and 6B) (Guan W, Wang G, Scott S A, et al. Shh influences cell number and the distribution of neuronal subtypes in dorsal root ganglia. Dev Biol 2008; 314:317-28). As shown in the figures, the RT-PCR analysis showed specific expression of Ngn2 in the AMS-RA treated cultures (A) and Patch1 in response to AMS Purm treated cultures.

We thus show that RA delivered with mesoporous silica has a similar effect as direct administration of RA on neuronal differentiation and neurite outgrowth in vitro of bNCSCs.

Example 3: Differentiation and Migration of NCSCs in the Presence of AMS Under the Kidney Capsule Background: We previously showed that NCSCs transplanted under the kidney capsule of one pole of the kidney extensively migrate towards co-transplanted pancreatic islets placed in the opposite pole of the same kidney (Olerud J, Kanaykina N, Vasylovska S, et al. Neural crest stem cells increase beta cell proliferation and improve islet function in co-transplanted murine pancreatic islets. Diabetologia 2009; 52:2594-601. Erratum in: Diabetologia. 2010; 53:396. Vasilovska, S [corrected to Vasylovska, S]; Kozlova E N, Jansson L. Differentiation and migration of neural crest stem cells are stimulated by pancreatic islets. Neuroreport 2009; 20:833-8). The purpose of these previous studies was to develop a new protocol for improved outcome after transplantation of pancreatic islets. Transplantation of pancreatic islets is an established therapy in selected patients with type 1 diabetes. The survival of transplanted islets is however insufficient and ways to improve their survival need to be developed. Co-transplanted NCSCs, which are able to secrete trophic factors and have potential to re-innervate transplanted islets may be a useful approach to improve the clinical outcome from islet transplantation. Our results showed that bNCSCs migrate towards islets, strongly promote their function and increase proliferation of beta-cells. However transplanted bNCSCs did not differentiate to functional neurons and did not re-innervate transplanted islets. Thus the development of protocols for NCSC differentiation in vivo is an important objective. The use of AMS containing morphogens may facilitate differentiation of bNCSCs in vivo after transplantation. Before embarking on long-term experiments we investigated whether AMS may have a negative effect on survival of bNCSCs grafted under the kidney capsule and their migration towards pancreatic islets grafted to the opposite pole of the same kidney.

Material and Methods:

We transplanted AMS–RA in one pole of the kidney together with bNCSCs and pancreatic islests in the opposite pole of the kidney (see FIGS. 7A-7(C)).

FIGS. 7A-7C are an overview of kidney with three different combinations of transplants:
- left (FIG. 7A): NCSCs (white circles) transplants located in the low pole of the kidney. NCSCs do not migrate from their location;
- middle (FIG. 7B): NCSCs migrate towards Islets (oval) which are transplanted on another side of the kidney;
- right (FIG. 7C): the reduced migration of NCSCs (small circles) towards Islets and increased differentiation of NCSCs in the initial location when they were co-transplanted with AMS (black triangle).

The islets were collected from transgenivc mice containing red fluorescent protein (RFP) and bNCSCs were prepared from the eGFP transgenic mice. The transplantation was performed as previously described (Olerud J, Kanaykina N, Vasylovska S, et al. Neural crest stem cells increase beta cell proliferation and improve islet function in co-transplanted murine pancreatic islets. Diabetologia 2009; 52:2594-601. Erratum in: Diabetologia. 2010; 53:396. Vasilovska, S [corrected to Vasylovska, S]; Kozlova E N, Jansson L. Differentiation and migration of neural crest stem cells are stimulated by pancreatic islets. Neuroreport 2009; 20:833-8) and after one month mice were perfused with fixative, their kidneys collected, postfixed for 4 hours, stored overnight in cold phosphate buffer containing 15% sucrose. The next day serial 14 µm cryostat sections were prepared through the whole organ.

Results:

AMS did not negatively affect survival of bNCSCs nor their migration towards pancreatic islets (FIGS. 7A-7C, 8A(i)-8A(iii) and 8B(i)-8B(ii)).

FIGS. 8A(i)-8(A)(iii) and 8(B)(i)-8B(ii) show eGFP-expressing bNCSC under the kidney capsule:
- A: migrated bNCSCs (left column) (FIG. 8A(i)) towards RFP-expressing pancreatic islets (middle column) (FIGS. 8A(ii)-8(A)(iii)) in the other pole of the kidney.
- B: left (FIG. 8B(i))—bNCSC transplanted without AMS, right (FIG. 8B(ii))—bNCSCs co-transplanted with AMS.

Based on the morphology of NCSCs appears that NCSC co-transplanted with particles are more differentiated compare to NCSCs transplanted alone (FIGS. 8A(i)-8B(ii)).

Example 4: Investigation Whether AMS Influences Glial Scar Formation after Brain Injury Background: Glial scar formation after injury to the brain or spinal cord represents a major cause for the inability of damaged axons to regenerate in the CNS. The consequences of these injuries are therefore permanent loss of functions which were served by the damaged neuronal systems. To reduce glial scar formation is important in order to promote axonal regeneration and restore lost functions.

We previously showed that glial scar formation in the brain connected with the expression of the calcium-binding protein Mts1/S100A4 which is produced specifically in white matter astrocytes. Down-regulation of Mts1/S100A4 in astrocytes reduced glial scar formation and increased their motility whereas up-regulation of Mts1/S100A4 expression resulted in increased glial scar formation (Fang Z, Duthoit N, Wicher G, et al. Intracellular calcium-binding protein S100A4 influences injury-induced migration of white matter astrocytes. Acta Neuropathol 2006; 111:213-9).

Here we investigate whether AMS and AMS+RA affect the extent of glial scar formation one week after injury to the cerebral cortex.

Material and Methods: We made an injury of a defined diameter and depth with a xx gauge needle in the frontal cerebral cortex of adult rats. In some of these cases implanted AMS or AMS–RA in the cavity. One week after injury the rats were perfused (see example 1), the brains were removed, postfixed, cryoprotected and cryosectioned in the coronal plane. The staining was performed for bTUB-neuronal marker (the same as above), glial fibrillary acidic protein (GFAP)-glial marker (see Example 2) and Mts1/S100A4 white matter astrocytes marker (gift from Lukanidin, 1:700, rabbit polyclonal), ED1-microglial marker (monoclonal, 1:500).

Results: Our in vitro data showed that AMS and AMS–RA reduces glial differentiation (FIGS. 5A(i)-5A(iii) and 5B). We thus were curious if AMS affects glial scar formation after cortical injury. The pilot experiment shows that glial response in the brain to the injury treated or not treated with AMS and AMS–RA differs from the response in untreated animals (see FIGS. 9A-9D).

FIGS. 9A-9D shows coronal sections through the rat cerebral cortex one week after a focal injury.
- Upper panel (FIG. 9B)—the injury without treatment;
- middle panel (FIG. 9C)—the injury+AMS;
- lower panel (FIG. 9D)—the injury+AMS–RA.

GFAP (glial marker) first column, OX42 (microglial marker) second column, Hoechst nuclear staining third column. Note the increased microglial reaction (second column) and reduced astroglial reaction (first column) in the treated injury sites (middle and lowest panels).

Our pilot experiments show that AMS decreases glial scar formation and induces microglial reaction in the injured areas. Further experiments will show if reduced glial scar formation is a direct effect of AMS or is a consequence of increased microglial reaction.

Example 5

We estimated the length of axons in the transplants treated with mesoporous particles of type NLAB-Silica(200) with pore size distribution centered on 200 Å and disordered pore structure, loaded with mimetics compared to non-treated transplants. The length of axons was calculated with the previously described method (Rønn L C, Ralets I, Hartz B P, Bech M, Berezin A, Berezin V, Møller A, Bock E. A simple procedure for quantification of neurite outgrowth based on stereological principles. J Neurosci Methods. 2000 Jul. 31; 100(1-2):25-32). The length of axons in mimetic treated transplants was 5 times greater than in untreated transplants (data not shown).

For evaluation of transplant size and neural stem/progenitor cell survival the HB9-EGFP expressing cells were analysed on every 5th section.

The NIH software ImageJ (Rasband, 1997, available at rsb.inb.nih.gov/ii) was used to measure transplant areas. The transplant volume estimate was calculated according to the formula A=TK[Σ(S1 to Sn)], where T is the thickness of the section (T=12 µm), K is the number of sections between the measured areas (K=50) and S is the area of the transplant on the sections from 1 to N. The evaluation demonstrated that the volume of mimetic-treated transplants was significantly increased (3×, p<0.5).

Figure 10:
FIG. 10 shows structural and textural properties of NLAB-Silica (200) including a SEM image of the disordered pore structure.
Figure 11:
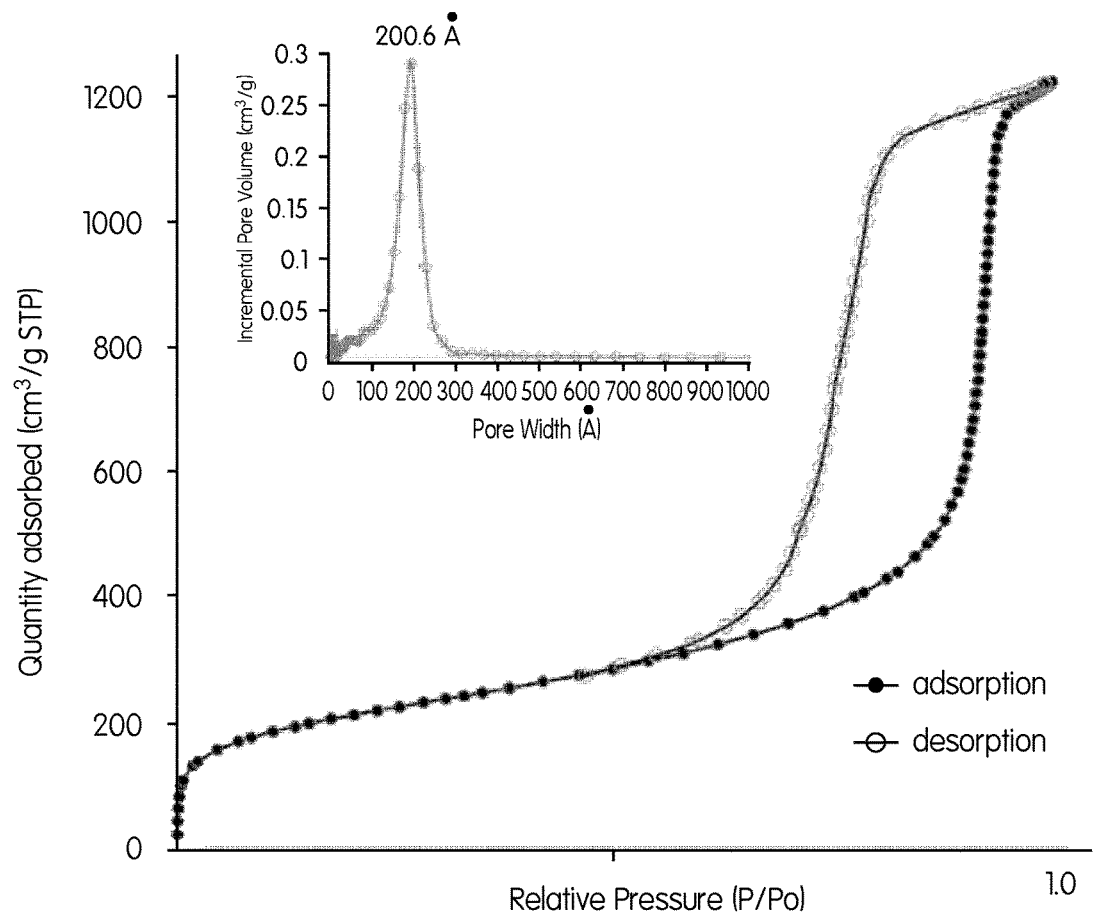
FIG. 11 shows structural and textural properties of NLAB-Silica (200) including a nitrogen adsorption isotherm and pore size distribution.
Figure 12A:
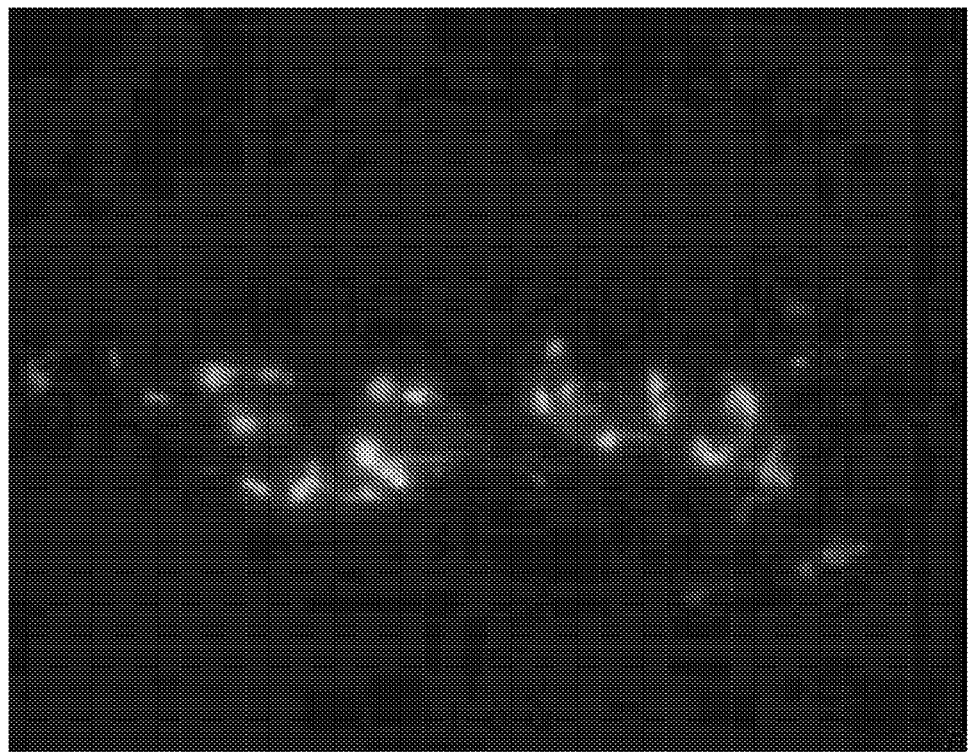
FIG. 12A shows the volume of untreated transplants loaded with peptide mimics.
Figure 12B:
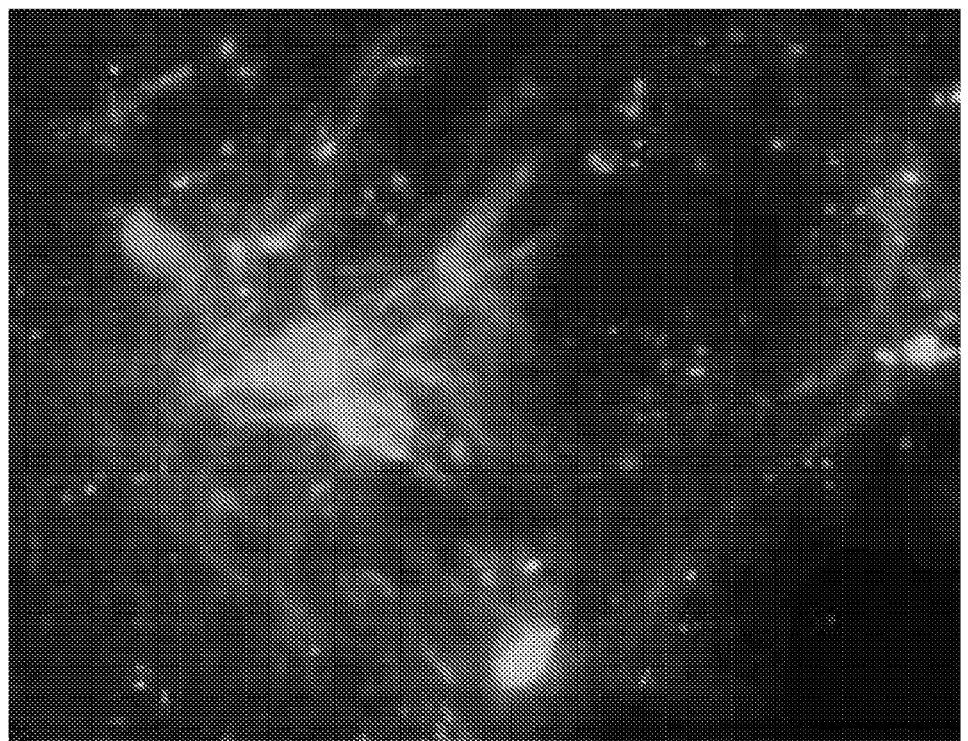
FIG. 12B shows the volume of transplants treated with NLAB-Silica (200) loaded with peptide mimics

The release properties of factors loaded into mesoporous material NLAB-Silica (200) were as follows: GDNF release in vivo: (Kirik D, Georgievska B, Rusenblad C, Bjorklund A. Delayed infusion of GDNF promotes recovery of motor function in the partial lesion model of Parkinson's disease. EJN, 2001, v13, p.1589-99) 0.25 µg/µl for 2 weeks infusion rate 0.5 µl per hour), i.e. 6 µg/day of GDNF. This release rate was achieved during 14 days. CNTF release in vivo: (Kelleher M O, Myles L M, Al-Abri R K, Glasby M A The use of Ciliary neurotrophic factor to promote recovery after peripheral nerve injury by delivering it at the site of the cell body. Acta Neurochir (Wien) 2006, v146, p.55-61) 100 µg/ml for 4 weeks 2.5 µl per hour, i.e. 6 µg/day of CNTF. This release rate was achieved during 14 days. FIGS. 10 and 11 show the structural and textural properties of NLAB-Silica (200), including SEM image (FIG. 10) of the disordered pore structure, and nitrogen adsorption isotherm and pore size distribution (FIG. 11). The volume of transplants treated with NLAB-Silica (200) loaded with peptide mimics (see FIG. 12B) was about 4 times larger than untreated ones (see FIG. 12A), and HB9-EGFP cells in treated transplants were on an average 8 times larger compared to cells in untreated transplants.

The invention claimed is:

1. A method for inducing neuron differentiation in stem cells selected from the group consisting of: embryotic stem cell (ESC)s, induced pluripotent stem cells (IPS cells), neural crest stem, cells (NCSC), and HB9-EGFP cells, comprising the consecutive steps of:
    (a) preparing a mesoporous silica,
    (b) loading said silica with factors selected from, the group consisting of: retinoic acid (RA), purmorphamine (PUR), glial-derived neurotrophic factor (GDNF), ciliary neurotrophic factor (CNTF) and mimetics thereof, and
    (c) performing a step selected from the group consisting of: (i) co-transplanting the loaded silica and said cells or transplanting a mixture of the loaded silica with said cells in a dorsal root ganglion or a frontal cerebral cortex of a rat, (ii) co-transplanting the loaded silica and said cells or transplanting a mixture of the loaded silica with said cells together with pancreatic islets in a kidney of a mouse, and (iii) mixing the loaded silica with said cells.

2. The method according to claim 1, for inducing neuron differentiation in human (h)embryotic stem cell (ESC)s, comprising the consecutive steps of:
    (a) preparing an anionic-surfactant-tempered mesoporous silica,
    (b) loading said silica with factors selected from the group consisting of: retinoic acid (RA) and purmorphamine (PUR),
    (c) mixing the loaded silica with the (h)embryotic stem cell (ESC)s, and
    (d) transplanting the mixture obtained in step (c) into a dorsal root ganglion of a rat.

3. The method according to claim 1, for inducing neuron differentiation in neural crest stem cells (NCSC) comprising the consecutive steps of:
    (a) preparing an anionic-surfactant-tempered mesoporous silica,
    (b) loading said silica with retinoic acid (RA), and
    (c) mixing the loaded silica with cultured neural crest stem cells (NCSC).

4. The method according to claim 1, for inducing neuron differentiation in neural crest stem cells (NCSC) comprising the consecutive steps of:
    (a) preparing an anionic-surfactant-tempered mesoporous silica,
    (b) loading said silica with retinoic acid (RA), and
    (c) transplanting the loaded silica in one pole of a kidney from a mouse and cotransplanting neural crest stem cells (NCSC) together with pancreatic islets in an opposite pole of the kidney of the mouse.

5. The method according to claim 1, for inducing neuron differentiation in neural crest stem cells (NCSC) comprising the consecutive steps of:
    (a) preparing an anionic-surfactant-tempered mesoporous silica,
    (b) loading said silica with retinoic acid (RA), and
    (c) transplanting the loaded silica in a frontal cerebral cortex of a rat.

6. The method according to claim 1, for inducing neuron differentiation in HB9-EGFP cells comprising the consecutive steps of:
    (a) preparing mesoporous silica particles having pore size distribution centered on 200A and disordered pore structure,
    (b) loading said silica particles with factors selected from the group consisting of: glial-derived neurotrophic factor (GDNF), ciliary neurotrophic factor (CNTF) and mimetics thereof, and
    (c) mixing the loaded silica particles with the HB9-EGPP cells.

7. The method according to claim 1, wherein said mesoporous silica has an average particle size and/or sizes in the range between 50-5000 nm.

8. The method according to claim 1, wherein the mesoporous silica has a particle shape comprising spheres or rod-shaped particles.

9. A method for inducing neuron differentiation in stem cells selected from the group consisting of: human (h)embryotic stem cell (ESC)s, neural crest stem cells (NCSC) and HB9-EGFP cells, comprising the consecutive steps of:
 (a) preparing a mesoporous silica,
 (b) loading said silica with factors selected from the group consisting of: retinoic acid (RA), purmorphamine (PUR), glial-derived neurotrophic factor (GDMF), ciliary neurotrophic factor (CNTF) and mimetics thereof, and
 (c) preforming a step selected from the group consisting of: (i) co-transplanting the loaded silica and said cells or transplanting a mixture of the loaded silica with said cells in a dorsal root ganglion or a frontal cerebral cortex of a rat, (ii) co-transplanting the loaded silica and said cells or transplanting a mixture of the loaded silica with said cells together with pancreatic islets in a kidney of a mouse, and (iii) mixing the loaded silica with said cells.

10. The method according to claim 9, for inducing neuron differentiation in human (h)embryotic stem cell (ESC)s, comprising the consecutive steps of:
 (a) preparing an anionic-surfactant-tempered-mesoporous silica,
 (b) loading said silica with factors selected from the group consisting of: retinoic acid (RA) and purmorphamine (PUR),
 (c) mixing the loaded silica with the (h)embryotic stem, cell (ESC)s, and
 (d) transplanting the mixture obtained in step (c) into a dorsal root ganglion of a rat.

11. The method according to claim 9, for inducing neuron differentiation in neural crest stem cells (NCSC) comprising the consecutive steps of:
 (a) preparing an anionic-surfactant-tempered mesoporous silica,
 (b) loading said silica with retinoic acid (RA), and
 (c) mixing the loaded silica with cultured neural crest stem cells (NCSC).

12. The method according to claim 9, for inducing neuron differentiation in neural crest stem cells (NCSC) comprising the consecutive steps of:
 (a) preparing an anionic-surfactant-tempered mesoporous silica,
 (b) loading said silica with retinoic acid (RA), and
 (c) transplanting the loaded silica in one pole of a kidney from a mouse and cotransplanting neural crest stem cells (NCSC) together with pancreatic islets in an opposite pole of the kidney of the mouse.

13. The method according to claim 9, for inducing neuron differentiation in neural crest stem cells (NCSC) comprising the consecutive steps of:
 (a) preparing an anionic-surfactant-tempered mesoporous silica,
 (b) loading said silica with retinoic acid (RA), and
 (c) transplanting the loaded silica in a frontal cerebral cortex of a rat.

14. The method according to claim 9, for inducing neuron differentiation in HB9-EGFP cells comprising the consecutive steps of:
 (a) preparing mesoporous silica particles having pore size distribution centered on 200A and disordered pore structure,
 (b) loading said silica particles with factors selected from the group consisting of: glial-derived neurotrophic factor (GDNF), ciliary neurotrophic factor (CNTF) and mimetics thereof, and
 (c) mixing the loaded silica particles with the HB9-EGPP cells.

15. The method according to claim 9, wherein said mesoporous silica has an average particle size and/or sizes in the range between 50-5000 nm.

16. The method according to claim 9, wherein the mesoporous silica has a particle shape comprising spheres or rod-shaped particles.

* * * * *